United States Patent [19]
Buynak et al.

[11] Patent Number: 6,156,745
[45] Date of Patent: Dec. 5, 2000

[54] 2β-SUBSTITUTED-6-ALKYLIDENE PENICILLANIC ACID DERIVATIVES AS β-LACTAMASE INHIBITORS

[75] Inventors: John D. Buynak, Dallas, Tex.; Akireddy Srinivasa Rao, Waukegan, Ill.; Venkata Ramana Doppalapudi, Dallas, Tex.

[73] Assignee: Research Corporation Technologies, Inc., Tucson, Ariz.

[21] Appl. No.: 09/223,077

[22] Filed: Dec. 29, 1998

Related U.S. Application Data

[60] Provisional application No. 60/070,240, Dec. 29, 1997.

[51] Int. Cl.[7] .................. C07D 499/87; A61K 31/43; A61D 31/04; C12N 9/99
[52] U.S. Cl. .................. 514/192; 514/195; 514/196; 514/197; 540/310
[58] Field of Search .................. 540/310; 514/192, 514/195, 196, 197

[56] References Cited

U.S. PATENT DOCUMENTS

| | | | |
|---|---|---|---|
| 5,597,817 | 1/1997 | Buynak et al. | 514/200 |
| 5,629,306 | 5/1997 | Buynak et al. | 514/206 |
| 5,681,563 | 10/1997 | Buynak et al. | 424/114 |
| 5,760,027 | 6/1998 | Buynak et al. | 514/200 |

FOREIGN PATENT DOCUMENTS

| | | |
|---|---|---|
| 0050805 | 5/1982 | European Pat. Off. . |
| 0150984 | 8/1985 | European Pat. Off. . |
| 0367606 | 5/1990 | European Pat. Off. . |
| 0043546 | 1/1992 | European Pat. Off. . |
| 2708219 | 9/1977 | United Kingdom . |
| 98/24793 | 6/1998 | WIPO . |

OTHER PUBLICATIONS

John D. Roberts and Marjorie C. Caserio, "Basic Principles of Organic Chemistry", Benjamin, New York, 1964, p. 405 & 537.

C. David Gutsche "The Chemistry of Carbonyl Compounds", Prentice–Hall, Englewood Cliffs, NJ, p. 46–47.

Abd El–Nabi, H.A., "Novel Heterocycles: A convenient Synthesis of Pyrrolo [2,3–d] pyrazole; Cycloaddition reaction of N–aryl (methyl) pyrrol–2,3–Diones to diazomethane and olefins", *Tetrahedron*, 53(5), 1813–1822, (Feb. 1997).

Arisawa, M., et al., "6–Acetylmethylenepenicillanic Acid (Ro 15–1903), A Potent β–Lactamase Inhibitor. I. Inhibition of Chromosomally and R–Factor–Mediated β–Lactamases", *The Journal of Antibiotics*, 35(11), 1578–1583, (Nov. 1982).

(List continued on next page.)

*Primary Examiner*—Mark L Berch
*Assistant Examiner*—Thomas McKenzie
*Attorney, Agent, or Firm*—Schwegman, Lundberg, Woessner & Kluth, P.A.

[57] ABSTRACT

Compounds of formula I:

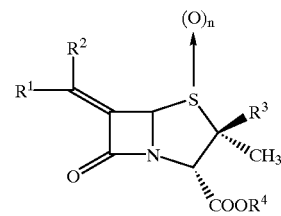

wherein $R^1$, $R^2$, $R^3$, $R^4$ and n have any of the values defined in the specification, and their pharmaceutically acceptable salts, are useful for inhibiting β-lactamase enzymes, for enhancing the activity of β-lactam antibiotics, and for treating β-lactam resistant bacterial infections in a mammal. The invention also provides pharmaceutical compositions, processes for preparing compounds of formula I, and novel intermediates useful for the synthesis of compounds of formula I.

20 Claims, 8 Drawing Sheets

OTHER PUBLICATIONS

Bennett, I.S., et al., "6–(Substituted Methylene) Penems, Potent Broad Spectrum Inhibitors of Bacterial β–Lactamase. V. Chiral 1,2,3–Triazolyl Derivatives", *The Journal of Antibiotics*, 44(9), 969–978, (Sep. 1991).

Brenner, D.G., et al., "6–(Methoxymethylene) penicillanic Acid: Inactivator of RTEM β–Lactamase from *Escherichia coli*", *Biochemistry*, 23(24), 5839–5846, (Nov. 20, 1984).

Buynak, J.D., et al., "Synthesis and biological activity of 7–alkylidenecephems", *J. Med. Chem.*, 38, 1022–1034, (1995).

Buynak, J.D., et al., "Synthesis and mechanistics evaluation of 7–vinylidenedephem sulfones as β–lactamase inhibitors", *J. of Am. Chem. Soc.*, 116, 10955–10965, (1994).

Buynak, J.D., et al., "Synthesis of 6–vinylidenepenams", *The Journal of Organic Chemistry*, 58 (6), 1325–1335, (Mar. 12, 1993).

Buynak, J.D. et al., "The Synthesis and lactamase Inhibitory Activity of 6–(Carboxymethylene) Pencillins and 7–(Carboxymethylene) Cephalosporins", *Bioorganic& Medicinal Chemistry Letters*, 5 (14), 1513–1518, (1995).

Chen, Y.L., et al., "Synthesis of a Potent β–Lactamase Inhibitor–1,1–Dioxo–6–(2–Pyridyl) Methylenepenicillanic Acid and its Reaction with Sodium methoxide", *Tetrahedron Letters*, 27 (30), 3449–3452, (1986).

Hagiwara, D., et al., "An Efficient Synthesis of 6–Oxopenicillanic and 7–Oxocephalosporanic Acid Derivatives", *Journal of the Chemical Society Chemical Communications*, 11, 578–579, (Jun. 1, 1982).

Kant, J., et al., "Diastereoselective Addition of Grignard Reagents to Azetidine–2,3–dione: Synthesis of Novel Taxol Analogues", *Tetrahedron Letters*, 37 (36), 6495–6498, (Sep. 2, 1996).

Kollenz, G., et al., "Reactions of Cyclic Oxalyl Compounds—38. New Isoindigoide Dyes from Heterocyclic 2,3–Diones—Synthesis and Thermal Rearrangement", *Tetrahedron*, 52 (15), 5427–5440, (Apr. 1996).

Martin, M.G., et al., "Epoxides as Alkene Protecting Groups. A Mild and Efficient Deoxygenation", *Tetrahedron Letters*, 25 (3), 251–254, (1984).

Palomo, C., et al., "New Synthesis of α–Amino Acid N–Carboxy Anhydrides through Baeyer–Villiger Oxidation of α–Keto β–Lactams", *The Journal of Organic Chemistry*, 59 (11), 3123–3130, (Jun. 3, 1994).

van der Veen, J.M., et al., "Synthesis of Azetidine–2,3–diones (α–Keto β–Lactams) via 3–(Phenylthio) –2–azetidinones", *The Journal of Organic Chemistry*, 54 (24), 5758–5762, (Nov. 24, 1989).

Clavulanic Acid

Tazobactam

9

2β-SUBSTITUTED-6-ALKYLIDENE PENICILLANIC ACID DERIVATIVES AS β-LACTAMASE INHIBITORS

PRIORITY OF INVENTION

This application claims priority of invention under 35 U.S.C. §119(e) from U.S. Provisional Application Number 60/070,240, filed Dec. 29, 1997.

BACKGROUND OF THE INVENTION

The most important mechanism of microbial resistance to β-lactam antibiotics is the bacterial production of β-lactamases, enzymes which hydrolytically destroy β-lactam antibiotics, such as penicillins and cephalosporins. This type of resistance can be transferred horizontally by plasmids that are capable of rapidly spreading the resistance, not only to other members of the same strain, but even to other species. Due to such rapid gene transfer, a patient can become infected with different organisms, each possessing the same β-lactamase.

β-lactamase enzymes have been organized into four molecular classes: A, B, C and D based on amino acid sequence. Class A, includes RTEM and the β-lactamase of *Staphylococcus aureus*, class C, includes the lactamase derived from P99 *Enterobacter cloacae*, and class D are serine hydrolases. Class A enzymes have a molecular weight of about 29 kDa and preferentially hydrolyze penicillins. The class B lactamases are metalloenzymes and have a broader substrate profile than the proteins in the other classes. Class C enzymes include the chromosomal cephalosporinases of gram-negative bacteria and have molecular weights of approximately 39 kDa. The recently recognized class D enzymes exhibit a unique substrate profile that differs significantly from the profile of both class A and class C enzymes.

The class C cephalosporinases, in particular, are responsible for the resistance of gram-negative bacteria to a variety of both traditional and newly designed antibiotics. The Enterobacter species, which possesses a class C enzyme, is now the third greatest cause of nosocomial infections in the United States. This class of enzymes often has poor affinities for inhibitors of the class A enzymes, such as clavulanic acid, a commonly prescribed inhibitor, and to common in vitro inactivators, such as 6-β-iodopenicillanate.

One strategy for overcoming this rapidly evolving bacterial resistance is the synthesis and administration of β-lactamase inhibitors. Frequently, β-lactamase inhibitors do not possess antibiotic activity themselves and are thus administered together with an antibiotic. One example of such a synergistic mixture is "AUGMENTIN" (a registered trademark of Smithkline Beecham Inc), which contains the antibiotic amoxicillin and the β-lactamase inhibitor, clavulanic acid.

Thus, there is a continuing need for novel β-lactamase inhibitors.

SUMMARY OF THE INVENTION

The present invention provides novel penicillin derivatives that are potent inhibitors of β-lactamase enzymes. Accordingly, the invention provides a compound of formula (I):

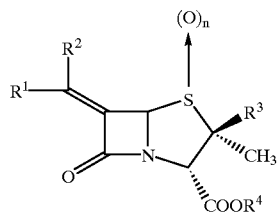

wherein $R^1$ and $R^2$ are each independently hydrogen, $(C_1-C_{10})$ alkyl, $(C_3-C_8)$cycloalkyl, $(C_2-C_{10})$alkenyl, $(C_2-C_{10})$ alkynyl, —$COOR_a$, —$CONR_bR_c$, cyano, —$C(=O)R_d$, —$OR_e$, aryl, heteroaryl, oxazolidinyl, isoxazolidinyl, morpholinyl, —$S(O)_mR_f$, —$NR_gR_h$, azido, or halo;

$R^3$ is $(C_3-C_{10})$alkyl, $(C_2-C_{10})$alkenyl, $(C_2-C_{10})$alkynyl, $(C_1-C_{10})$alkanoyl, $(C_3-C_8)$cycloalkyl, aryl, heteroaryl, aryl$(C_1-C_{10})$alkyl, heteroaryl$(C_1-C_{10})$alkyl, or —$CH_2R_i$, wherein $R_i$ is halo, cyano, cyanato, —$OR_j$, —$NR_kR_l$, azido, —$SR_m$, or $(C_3-C_8)$cycloalkyl;

$R^4$ is hydrogen, $(C_1-C_{10})$alkyl, $(C_3-C_8)$cycloalkyl, $(C_2-C_{10})$alkenyl, $(C_2-C_{10})$alkynyl, aryl, or heteroaryl;

m and n are each independently 0, 1, or 2;

each $R_a-R_f$ is independently hydrogen, $(C_1-C_{10})$alkyl, $(C_3-C_8)$cycloalkyl, $(C_2-C_{10})$alkenyl, $(C_2-C_{10})$alkynyl, aryl, heteroaryl, oxazolidinyl, isoxazolidinyl, or morpholinyl;

each $R_g$ or $R_h$ is independently hydrogen, $(C_1-C_{10})$alkyl, $(C_3-C_8)$cycloalkyl, $(C_2-C_{10})$alkenyl, $(C_2-C_{10})$alkynyl, $(C_1-C_{10})$alkanoyl, aryl, benzyl, phenethyl, heteroaryl oxazolidinyl, isoxazolidinyl, or morpholinyl; or $R_g$ and R$h$ together with the nitrogen to which they are attached are triazolyl, imidazolyl, oxazolidinyl, isoxazolidinyl, pyrrolyl, morpholino, piperidino, pyrrolidino, pyrazolyl, indolyl, or tetrazolyl;

$R_j$ is hydrogen, $(C_1-C_{10})$alkyl, $(C_3-C_8)$cycloalkyl, $(C_2-C_{10})$alkenyl, $(C_2-C_{10})$alkynyl, —$C(=O)N(R_p)_2$, aryl, heteroaryl, arylcarbonyl, heteroarylcarbonyl, or $(C_1-C_{10})$alkanoyl, wherein each $R_p$ is independently hydrogen, $(C_1-C_{10})$alkyl, aryl, benzyl, phenethyl, or heteroaryl;

each $R_k$ or $R_l$ is independently hydrogen, $(C_1-C_{10})$alkyl, $(C_3-C_8)$cycloalkyl, $(C_2-C_{10})$alkenyl, $(C_2-C_{10})$ alkynyl, $(C_1-C_{10})$alkanoyl, —$C(=O)N(R_q)_2$, aryl, benzyl, phenethyl, heteroaryl oxazolidinyl, isoxazolidinyl, or morpholinyl, wherein each $R_q$ is independently hydrogen, $(C_1-C_{10})$alkyl, aryl, benzyl, phenethyl, or heteroaryl; or $R_k$ and $R_l$ together with the nitrogen to which they are attached are triazolyl, imidazolyl, oxazolidinyl, isoxazolidinyl, pyrrolyl, morpholino, piperidino, pyrrolidino, pyrazolyl, indolyl, or tetrazolyl; and $R_m$ is hydrogen, $(C_1-C_{10})$alkyl, $(C_3-C_8)$cycloalkyl, $(C_2-C_{10})$alkenyl, $(C_2-C_{10})$alkynyl, cyano, aryl, benzyl, phenethyl, heteroaryl, oxazolidinyl, isoxazolidinyl, or morpholinyl;

wherein any $(C_1-C_{10})$alkyl, $(C_3-C_8)$cycloalkyl, $(C_2-C_{10})$ alkenyl, $(C_2-C_{10})$alkynyl, $(C_1-C_{10})$alkanoyl, aryl, benzyl, phenethyl, heteroaryl, arylcarbonyl, heteroarylcarbonyl, oxazolidinyl, isoxazolidinyl, or morpholinyl of $R^1-R^4$, $R_a-R_m$, or $R_p-R_q$, may optionally be substituted with 1, 2, or 3 Z; and each Z is independently halo, nitro, cyano, hydroxy, $(C_1-C_{10})$ alkyl, $(C_3-C_8)$cycloalkyl, $(C_1-C_{10})$alkoxy, $(C_1-C_{10})$alkanoyl, $(C_2-C_{10})$alkanoyloxy, trifluoromethyl, aryl, aryloxy, heteroaryl, or —$SR_n$, wherein $R_n$ is hydrogen, $(C_1-C_{10})$alkyl, $(C_3-C_8)$cycloalkyl, aryl, benzyl, phenethyl, or heteroaryl;

and further wherein any aryl, aryloxy, heteroaryl, benzyl, or phenethyl of Z may optionally be substituted with 1, 2, or 3 substituents selected from the group consisting of halo, nitro, cyano, hydroxy, $(C_1-C_{10})$alkyl, $(C_3-C_8)$cycloalkyl, $(C_1-C_{10})$alkoxy, $(C_1-C_{10})$alkanoyl, $(C_1-C_{10})$alkanoyloxy, benzyloxy, 4-methoxybenzyloxy, and trifluoromethyl;

or a pharmaceutically acceptable salt thereof.

DETAILED DESCRIPTION OF THE INVENTION

Figure 1:
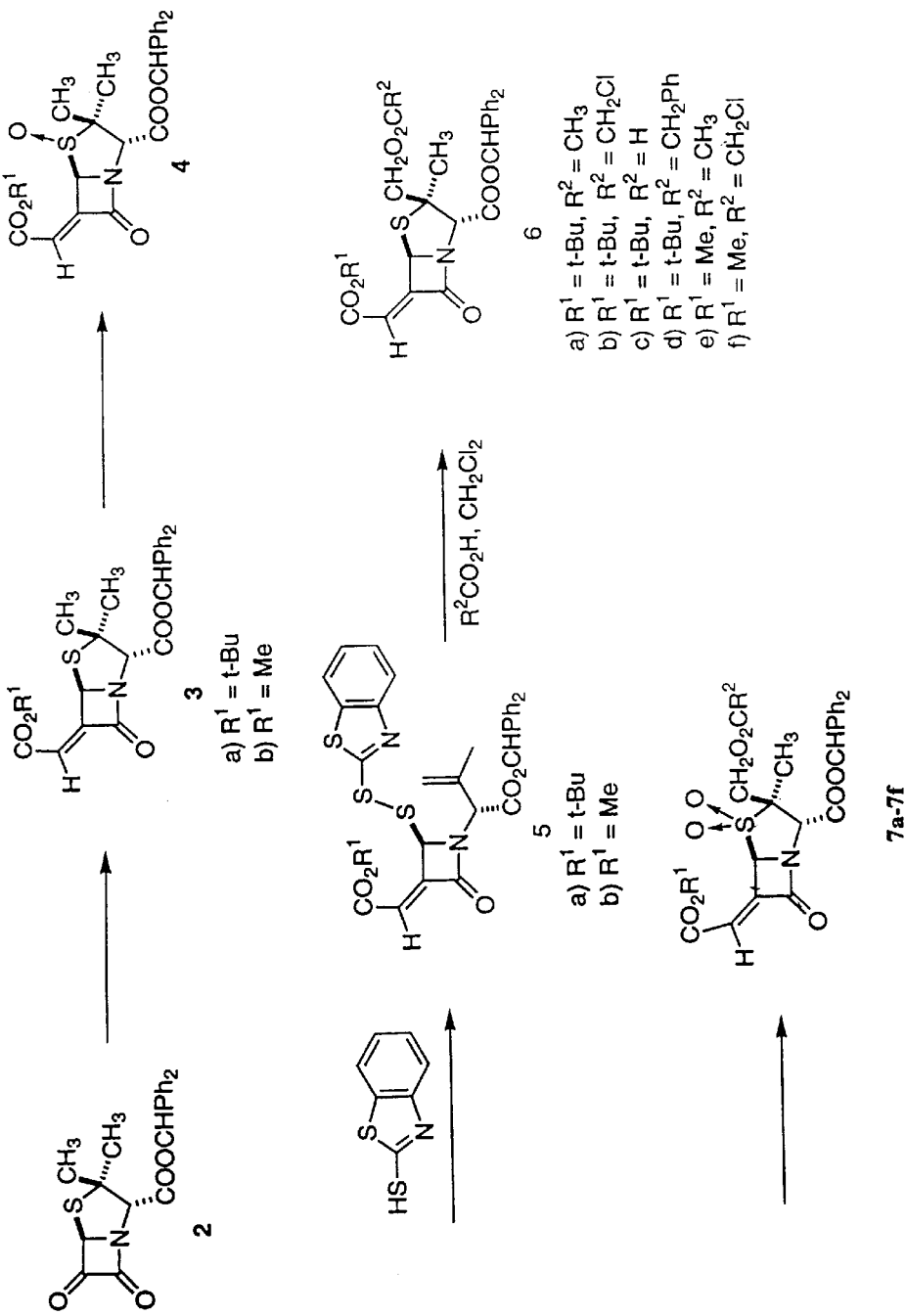
FIG. 1 illustrates the preparation of compounds of the invention.

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein each X is absent or is H, O, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having one or more chiral centers may exist and be isolated as optically active and racemic forms. Some compounds may exhibit polymorphism. It is to be understood that the present invention encompasses any racemic, optically-active, polymorphic, or stereoisomeric form, or mixtures thereof, of a compound of the invention, that possesses the useful properties described herein, it being well known in the art how to prepare optically active forms (for example, by resolution of the racemic form by recrystallization techniques, by synthesis, from optically-active starting materials, by chiral synthesis, or by chromatographic separation using a chiral stationary phase) and how to determine β-lactamase inhibitory activity using the tests described herein, or using other tests which are well known in the art. Preferably, the absolute stereochemistry of compounds of the invention is that shown in formula I.

Specific and preferred values listed below for radicals, substituents, and ranges, are for illustration only and they do not exclude other defined values or other values within defined ranges for the radicals and substituents.

Specifically, $(C_1-C_{10})$alkyl can be methyl, ethyl, propyl, isopropyl, butyl, iso-butyl, sec-butyl, pentyl, 3-pentyl, hexyl, heptyl, octyl, nonyl or decyl; $(C_3-C_8)$cycloalkyl can be cyclopropyl, cyclobutyl, cyclopentyl, cyclohexyl, cycloheptyl, or cyclooctyl; $(C_1-C_{10})$alkoxy can be methoxy, ethoxy, propoxy, isopropoxy, butoxy, iso-butoxy, sec-butoxy, pentoxy, 3-pentoxy, hexyloxy, heptyloxy, octyloxy, nonyloxy, or decyloxy; $(C_2-C_{10})$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, or 9-decenyl; $(C_2-C_{10})$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonylyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, or 9-decynyl; $(C_1-C_{10})$alkanoyl can be acetyl, propanoyl, butanoyl, isobutanoyl, pentanoyl, hexanoyl, heptanoyl, octanoyl, nonanoyl, or decanoyl; and $(C_2-C_{10})$alkanoyloxy can be acetoxy, propanoyloxy, butanoyloxy, isobutanoyloxy, pentanoyloxy, hexanoyloxy, heptanoyloxy, octanoyloxy, nonanoyloxy, or decanoyloxy. Specifically "aryl" can be phenyl, indenyl, or naphthyl. Specifically, "heteroaryl" can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), thiadiazolyl, thiatriazolyl, oxadiazolyl, or quinolyl (or its N-oxide). More specifically, "heteroaryl" can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide). More specifically, heteroaryl can be pyridyl.

Specifically, $R_a$ is methyl, ethyl, propyl, isopropyl, butyl, tert-butyl, pentyl, cyclopropyl, cyclopentyl, cyclohexyl, phenyl, toluoyl, anisoyl, mesityl, xylyl, or pyridinyl; $R^3$ is —$CH_2R_i$; $R_i$ is halo, cyano, cyanato, —$OR_j$, —$NR_kR_l$, azido, or —$SR_m$; and Z is halo, nitro, cyano, hydroxy, $(C_1-C_{10})$alkoxy, $(C_1-C_{10})$alkanoyl, $(C_2-C_{10})$alkanoyloxy, trifluoromethyl or —$SR_n$. More specifically, $R^3$ is acetoxymethyl, phenylacetoxymethyl, phenoxyacetoxymethyl, chloroacetoxymethyl, pyridylacetoxymethyl, triazolylacetoxymethyl, imidazolylacetoxymethyl, tetrazolylthioacetoxymethyl, or tetrazolylthioacetoxymethyl optionally substituted on the tetrazol ring with $(C_1-C_6)$alkyl, or aryl.

Another specific value for $R^3$ is acetoxynmethyl, chloroacetoxymethyl, formyloxymethyl, phenylacetoxymethyl, (1-methyl-1H-tetrazol-5-ylthio) acetoxymethyl, (3,4-dihydroxyphenyl)acetoxymethyl, 3,4-di(4-methoxybenzyloxy)phenylacetoxymethyl, chloromethyl, formyl, or 2-cyanovinyl.

A preferred value for $R^1$ is hydrogen; for $R^2$ is carboxy, tert-butoxycarbonyl, or methoxycarbonyl; for $R^3$ is acetoxymethyl, chloroacetoxymethyl, formyloxymethyl, phenylacetoxymethyl, (1-methyl-1H-tetrazol-5-ylthio) acetoxymethyl, (3,4-dihydroxyphenyl)acetoxymethyl, chloromethyl, formyl, or 2-cyanovinyl; for $R^4$ is hydrogen or diphenylmethyl; and for n is 2. A more preferred value for $R^3$ is acetoxymethyl, chloroacetoxymethyl, phenylacetoxymethyl, (3,4-dihydroxyphenyl)acetoxymethyl, or (1-methyl-1H-tetrazol-5-ylthio) acetoxynmethyl.

Another prefered value for $R^2$ is pyridyl (e.g. 2-pyridyl).

A preferred group of compounds are compounds of formula I wherein $R^3$ is —$CH_2OR_j$; or a pharmaceutically acceptable salt thereof.

Another preferred group of compounds are compounds of formula I wherein $R^3$ is —$CH_2OR_j$; and $R_j$ is $C_2$-alkanoyl, optionally substituted with halo, nitro, cyano, hydroxy, $(C_3-C_8)$cycloalkyl, $(C_1-C_{10})$alkoxy, $(C_1-C_{10})$alkanoyl, $(C_2-C_{10})$alkanoyloxy, trifluoromethyl, aryl, aryloxy, heteroaryl, or —$SR_n$; wherein $R_n$ is hydrogen, $(C_1-C_{10})$alkyl, $(C_3-C_8)$cycloalkyl, aryl, benzyl, phenethyl, or heteroaryl; and further wherein any aryl, aryloxy, heteroaryl, benzyl, or phenethyl may optionally be substituted with 1, 2, or 3 substituents selected from the group consisting of halo, nitro, cyano, hydroxy, $(C_1-C_{10})$alkyl, $(C_3-C_8)$cycloalkyl, $(C_1-C_{10})$alkoxy, $(C_1-C_{10})$alkanoyl, $(C_2-C_{10})$alkanoyloxy, and trifluoromethyl; or a pharmaceutically acceptable salt thereof.

A preferred compound is a compound of formula I wherein: $R^1$ and $R^2$ are each independently hydrogen, $(C_1-C_{10})$alkyl, $(C_3-C_8)$cycloalkyl, $(C_2-C_{10})$alkenyl, $(C_2-C_{10})$alkynyl, —$COOR_a$, —$CONR_bR_c$, cyano, —$C(=O)R_d$, —$OR_e$, aryl, heteroaryl, oxazolidinyl, isoxazolidinyl, morpholinyl, —$S(O)_mR_f$, —$NR_gR_h$, azido, or halo; $R^3$ is $(C_3-C_{10})$alkyl, $(C_2-C_{10})$alkenyl, $(C_2-C_{10})$alkynyl, $(C_1-C_{10})$alkanoyl, $(C_3-C_8)$cycloalkyl, aryl, heteroaryl, aryl$(C_1-C_{10})$alkyl, heteroaryl$(C_1-C_{10})$alkyl, or —$CH_2R_i$, wherein $R_i$ is halo, cyano, cyanato, —$OR_j$, —$NR_kR_l$, azido, —$SR_m$, or $(C_3-C_8)$cycloalkyl; $R^4$ is hydrogen, $(C_1-C_{10})$alkyl, $(C_3-C_8)$cycloalkyl, $(C_2-C_{10})$alkenyl, $(C_2-C_{10})$alkynyl, aryl, or heteroaryl; m and n are each independently 0, 1, or 2; each $R_a-R_f$ is independently hydrogen, $(C_1-C_{10})$alkyl, $(C_3-C_8)$cycloalkyl, $(C_2-C_{10})$alkenyl, $(C_2-C_{10})$alkynyl, aryl, heteroaryl, oxazolidinyl, isoxazolidinyl, or morpholinyl; each $R_g$ or $R_h$ is independently hydrogen, $(C_1-C_{10})$alkyl, $(C_3-C_8)$cycloalkyl, $(C_2-C_{10})$alkenyl, $(C_2-C_{10})$alkynyl, $(C_1-C_{10})$alkanoyl, aryl, benzyl, phenethyl, heteroaryl oxazolidinyl, isoxazolidinyl, or morpholinyl; or $R_g$ and $R_h$ together with the nitrogen to which they are attached are triazolyl, imidazolyl, oxazolidinyl, isoxazolidinyl, pyrrolyl, morpholino, piperidino, pyrrolidino, pyrazolyl, indolyl, or tetrazolyl; $R_j$ is hydrogen, $(C_1-C_{10})$alkyl, $(C_3-C_8)$cycloalkyl, $(C_2-C_{10})$alkenyl, $(C_2-C_{10})$alkynyl, —$C(=O)N(R_p)_2$, aryl, heteroaryl, arylcarbonyl, heteroarylcarbonyl, or $(C_1-C_{10})$alkanoyl, wherein each $R_p$ is independently hydrogen, $(C_1-C_{10})$alkyl, aryl, benzyl, phenethyl, or heteroaryl; each $R_k$ or $R_l$ is independently hydrogen, $(C_1-C_{10})$alkyl, $(C_3-C_8)$cycloalkyl, $(C_2-C_{10})$alkenyl, $(C_2-C_{10})$alkynyl, $(C_1-C_{10})$alkanoyl, —$C(=O)N(R_q)_2$, aryl, benzyl, phenethyl, heteroaryl oxazolidinyl, isoxazolidinyl, or morpholinyl, wherein each $R_q$ is independently hydrogen, $(C_1-C_{10})$alkyl, aryl, benzyl, phenethyl, or heteroaryl; or $R_k$ and $R_l$ together with the nitrogen to which they are attached are triazolyl, imidazolyl, oxazolidinyl, isoxazolidinyl, pyrrolyl, morpholino, piperidino, pyrrolidino, pyrazolyl, indolyl, or tetrazolyl; and $R_m$ is hydrogen, $(C_1-C_{10})$alkyl, $(C_3-C_8)$cycloalkyl, $(C_2-C_{10})$alkenyl, $(C_2-C_{10})$alkynyl, cyano, aryl, benzyl, phenethyl, heteroaryl, oxazolidinyl, isoxazolidinyl, or morpholinyl; wherein any $(C_1-C_{10})$alkyl, $(C_3-C_8)$cycloalkyl, $(C_2-C_{10})$alkenyl, $(C_2-C_{10})$alkynyl, $(C_1-C_{10})$alkanoyl, aryl, benzyl, phenethyl, heteroaryl, arylcarbonyl, heteroarylcarbonyl, oxazolidinyl, isoxazolidinyl, or morpholinyl of $R^1-R^4$, $R_a-R_m$, or $R_p-R_q$, may optionally be substituted with 1, 2, or 3 Z; and each Z is independently halo, nitro, cyano, hydroxy, $(C_1-C_{10})$alkyl, $(C_3-C_8)$cycloalkyl, $(C_1-C_{10})$alkoxy, $(C_1-C_{10})$alkanoyl, $(C_2-C_{10})$alkanoyloxy, trifluoromethyl, aryl, aryloxy, heteroaryl, or —$SR_n$, wherein $R_n$ is hydrogen, $(C_1-C_{10})$alkyl, $(C_3-C_8)$cycloalkyl, aryl, benzyl, phenethyl, or heteroaryl; and further wherein any aryl, aryloxy, heteroaryl, benzyl, or phenethyl of Z may optionally be substituted with 1, 2, or 3 substituents selected from the group consisting of halo, nitro, cyano, hydroxy, $(C_1-C_{10})$alkyl, $(C_3-C_8)$cycloalkyl, $(C_1-C_{10})$alkoxy, $(C_1-C_{10})$alkanoyl, $(C_2-C_{10})$alkanoyloxy, and trifluoromethyl; or a pharmaceutically acceptable salt thereof.

Another prefered compound is a compound of formula (I) wherein: $R^1$ is hydrogen; $R^2$ is $(C_1-C_{10})$alkyl, —$COOR_a$, —$CONR_bR_c$, cyano, —$C(=O)R_d$, —$OR_e$, aryl, heteroaryl, oxazolidinyl, isoxazolidinyl, morpholinyl, —$S(O)_mR_f$, —$NR_gR_h$, azido, or halo; $R^3$ is $(C_2-C_{10})$alkenyl, $(C_2-C_{10})$alkynyl, $(C_1-C_{10})$alkanoyl, or —$CH_2R_i$, wherein $R_i$ is halo, cyano, cyanato, —$OR_j$, —$NR_kR_l$, azido, —$SR_m$, or $(C_3-C_8)$cycloalkyl; $R^4$ is hydrogen, $(C_1C_{10})$alkyl, $(C_3-C_8)$cycloalkyl, $(C_2-C_{10})$alkenyl, $(C_2-C_{10})$alkynyl, aryl, or heteroaryl; m and n are each independently 0, 1, or 2; each $R_a-R_f$ is independently hydrogen, $(C_1-C_{10})$alkyl, $(C_3-C_8)$cycloalkyl, $(C_2-C_{10})$alkenyl, $(C_2-C_{10})$alkynyl, aryl, or heteroaryl; each $R_g$ or $R_h$ is independently hydrogen, $(C_1-C_{10})$alkyl, $(C_3-C_8)$cycloalkyl, $(C_2-C_{10})$alkenyl, $(C_2-C_{10})$alkynyl, $(C_1C_{10}$alkanoyl, aryl, benzyl, phenethyl, or or $R_g$ and $R_h$ together with the nitrogen to which they are attached are morpholino, piperidino, or pyrrolidino; $R_j$ is hydrogen, $(C_1-C_{10})$alkyl, $(C_3-C_8)$cycloalkyl, $(C_2-C_{10})$alkenyl, $(C_2-C_{10})$alkynyl, —$C(=O)N(R_p)_2$, aryl, heteroaryl, arylcarbonyl, heteroarylcarbonyl, or $(C_1-C_{10})$alkanoyl, wherein each $R_p$ is independently hydrogen, $(C_1-C_{10})$alkyl, aryl, benzyl, phenethyl, or heteroaryl; each $R_k$ or $R_l$ is independently hydrogen, $(C_1-C_{10})$alkyl, $(C_1-C_{10})$alkanoyl, aryl, benzyl, or phenethyl; or $R_k$ and $R_l$ together with the nitrogen to which they are attached are morpholino, piperidino, or pyrrolidino; and $R_m$ is $(C_1-C_{10})$alkyl, $(C_3-C_8)$cycloalkyl, $(C_2-C_{10})$alkenyl, or $(C_2-C_{10})$alkynyl; wherein any $(C_1-C_{10})$alkyl, $(C_1-C_{10})$alkanoyl, aryl, benzyl, phenethyl, heteroaryl, arylcarbonyl, or heteroarylcarbonyl of $R^1-R^4$, $R_a-R_m$, or $R_p$, may optionally be substituted with 1, 2, or 3 Z; and each Z is independently halo, nitro, cyano, hydroxy, $(C_1-C_{10})$alkyl, $(C_1-C_{10})$alkoxy, $(C_1-C_{10})$alkanoyl, $(C_2-C_{10})$alkanoyloxy, trifluoromethyl, aryl, aryloxy, heteroaryl, or —$SR_n$, wherein $R_n$ is hydrogen, $(C_1-C_{10})$alkyl, $(C_3-C_8)$cycloalkyl, aryl, benzyl, phenethyl, or heteroaryl; and further wherein any aryl, aryloxy, heteroaryl, benzyl, or phenethyl of Z may optionally be substituted with 1, 2, or 3 substituents selected from the group consisting of halo, nitro, cyano, hydroxy, $(C_1-C_{10})$ alkyl, $(C_1-C_{10})$alkoxy, $(C_1-C_{10})$alkanoyl, $(C_2-C_{10})$ alkanoyloxy, and trifluoromethyl; or a pharmaceutically acceptable salt thereof.

Processes and novel intermediates useful for preparing compounds of formula I are provided as further embodiments of the invention and are illustrated by the following procedures in which the meanings of the generic radicals are as given above unless otherwise qualified. Certain compounds of formula (I) are also useful as intermediates for preparing other compounds of formula (I).

A compound of formula I (wherein $R^1$ is hydrogen, $R^4$ is diphenylmethyl and n is 0, formula 6) can be prepared by treatment of a corresponding compound of formula 5 with silver acetate and the requisite carboxylic acid in dichloromethane, as illustrated in FIG. 1. The reaction can conveniently be carried out as described in Examples 1–6. In general, a compound of formula (I) can be prepared from a corresponding compound of formula 18 by treatment with a requsite acid of formula $R^2CO_2H$ in the presence of a suitable catalyst (e.g. silver acetate). The reaction can conveniently be carried out under conditions similar to those described in Examples 1–6 and 34 hereinbelow.

Figure 4:
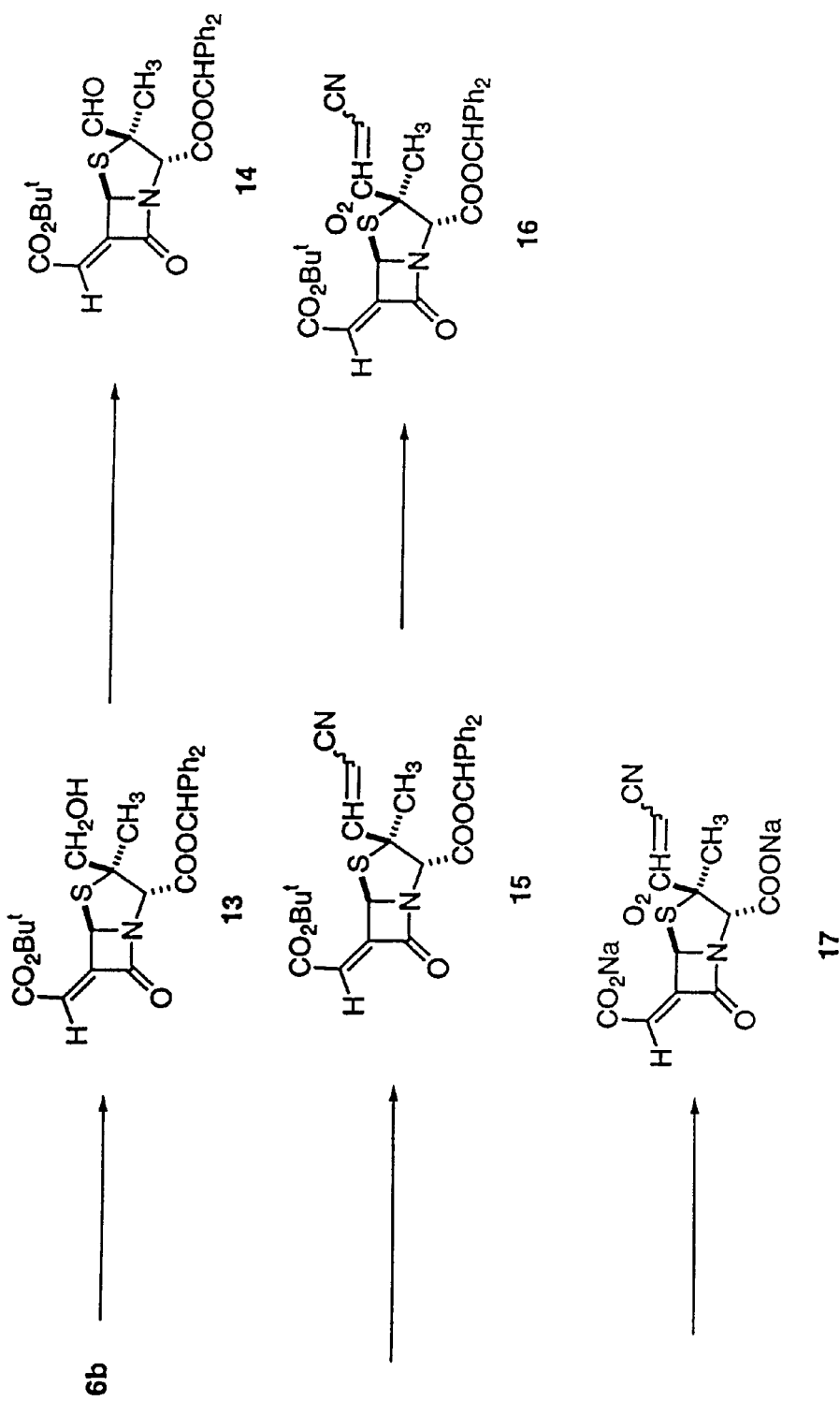
FIG. 4 illustrates the preparation of compounds of the invention.

A compound of formula I wherein $R^3$ is hydroxymethyl may also be prepared from a corresponding compound of formula I wherein $R^3$ is chloroacetoxymethyl by treatment with thiourea in the presence of a suitable base, such as for example, pyridine (T. Greene, P. Wutz "Protective Groups in Organic Synthesis, Second Edition; John Wiley and Sons, Inc.; New York, 1991, p. 92). The reaction can conveniently be carried out in a suitable solvent, such as dimethylformamide, as illustrated in FIG. 4 for the conversion of compound 6b to compound 13.

A compound of formula I wherein $R^3$ is halomethyl can be prepared from a corresponding compound of formula I wherein $R^3$ is hydroxymethyl using techniques that are well known in the art, for example techniques such as those described in Jerry March "Advanced Organic Chemistry" John Wiley & Sons, 4 ed. 1992, 431–433.

A compound of formula I wherein $R^3$ is cyanomethyl can be prepared from a corresponding compound of formula I wherein $R^3$ is halomethyl using techniques that are well known in the art, for example techniques such as those described in Jerry March "Advanced Organic Chemistry" John Wiley & Sons, 4 ed. 1992, 482.

A compound of formula I wherein $R^3$ is cyanatomethyl can be prepared from a corresponding compound of formula I wherein $R^3$ is hydroxymethyl by reaction with a cyanogen halide using techniques that are well known in the art, for example techniques such as those described in Jerry March "Advanced Organic Chemistry" John Wiley & Sons, 4 ed.1992, 387.

A compound of formula I wherein $R^3$ is —$CH_2OR_i$ can be prepared from a corresponding compound of formula I wherein $R^3$ is —$CH_2$(halo) by reaction with the requisite alcohol $HOR_i$ using techniques that are well known in the art, for example techniques such as those described in Jerry March "Advanced Organic Chemistry" John Wiley & Sons, 4 ed.1992, 386–387.

A compound of formula I wherein $R^3$ is —$CH_2NR_jR_k$ can be prepared from a corresponding compound of formula I wherein $R^3$ is —$CH_2$(halo) using techniques that are well known in the art, for example techniques such as those described in Jerry March "Advanced Organic Chemistry" John Wiley & Sons, 4 ed.1992, 411–413, 425–427.

A compound of formula I wherein $R^3$ is azidomethyl can be prepared from a corresponding compound of formula I wherein $R^3$ is —$CH_2$(halo) using techniques that are well known in the art, for example techniques such as those described in Jerry March "Advanced Organic Chemistry" John Wiley & Sons, 4 ed.1992, 411–413, 428–429.

A compound of formula I wherein $R^3$ is —$CH_2 SR_i$ can be prepared from a corresponding compound of formula I wherein $R^3$ is —$CH_2$(halo) by reaction with the requisite thiol $HSR_i$ using techniques that are well known in the art, for example techniques such as those described in Jerry March "Advanced Organic Chemistry" John Wiley & Sons, 4 ed. 1992, 407.

A compound of formula I wherein n is 2 (formula 7) can be prepared by oxidation of a corresponding compound of formula I wherein n is 0, for example, by using meta-chloroperbenzoic acid (mCPBA), as illustrated in FIG. 1 for the conversion of a compound of formula 6 to a compound of formula 7.

A compound of formula I wherein n is 1 can be prepared by oxidation of a corresponding compound of formula I wherein n is 0, using one equivalent of an acceptable oxidizing agent, for example, mCPBA.

Figure 2:
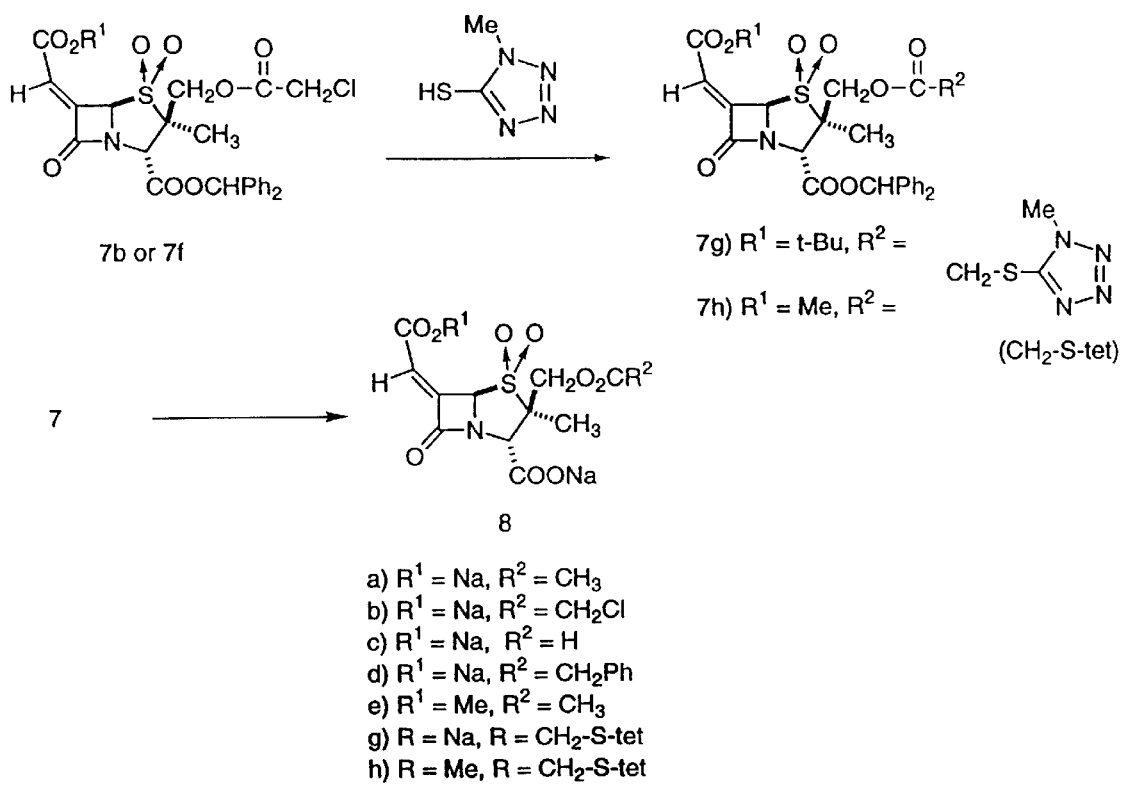
FIG. 2 illustrates the preparation of compounds of the invention.

A compound of formula I wherein $R^4$ is hydrogen can generally be prepared from a corresponding ester of formula I wherein $R^4$ is other than hydrogen by hydrolysis, using techniques which are well known in the art, as illustrated in FIG. 2 for the conversion of a compound of formula 7 to a compound of formula 8.

A compound of formula I wherein $R^2$ is carboxy can be prepared from a corresponding ester of formula I by hydrolysis, using techniques which are well known in the art, as illustrated in FIG. 2 for the conversion of a compound of formula 7 to a compound of formula 8.

A compound of formula I wherein $R^1$ is carboxy can be prepared from a corresponding ester of formula I by hydrolysis, using techniques which are well known in the art.

A compound of formula I wherein $R^3$ is (1-methyl-1H-tetrazol-5-yl)thioacetoxymethyl can be prepared from a corresponding compound of formula I wherein $R^3$ is chloroacetoxymethyl by reaction with 1-methyl-1H-tetrazol-5-ylmercaptan using techniques which are well known in the art, as illustrated in FIG. 2 for the conversion of a compound of formula 7b to a compound of formula 7g. For Example, the reaction can conveniently be carried out as described in Example 13 or 14.

Figure 3:
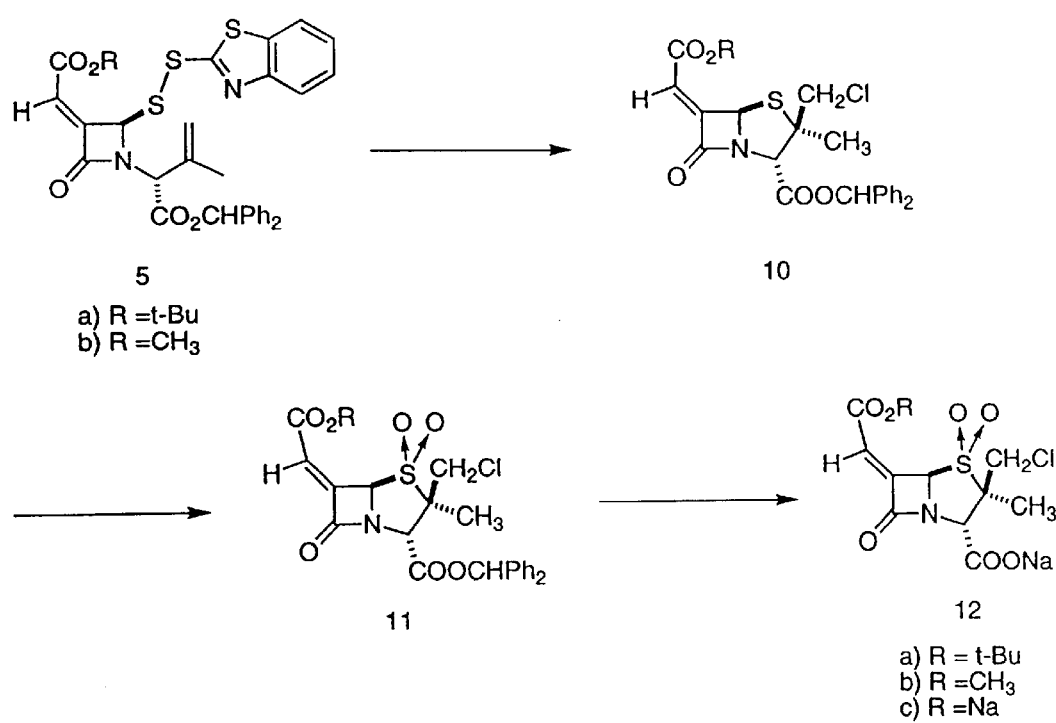
FIG. 3 illustrates the preparation of compounds of the invention.

A compound of formula I wherein $R^3$ is chloromethyl (formula 10) can be prepared from a corresponding compound of formula 5 as illustrated in FIG. 3, by treatment with copper II chloride in a suitable solvent. For example, the reaction can conveniently be carried out as described in Example 22 or 23.

A compound of formula I wherein $R^3$ is formyl can be prepared from a corresponding compound of formula I wherein $R^3$ is hydroxymethyl by oxidation, using techniques which are well known in the art, as illustrated in FIG. 4 for the conversion of a compound of formula 13 to a compound of formula 14. The reaction can conveniently be carried out by treating an alcohol of formula 13 with oxalyl chloride in the presence of dimethylsulfoxide and a suitable base, such as triethylamine, as described in Example 30.

A compound of formula I wherein $R^3$ is a 1-alkenyl substituent can generally be prepared from a corresponding compound of formula I wherein $R^3$ is formyl, by reaction with the requisite ylide or stabilized ylide, using techniques which are well known in the art, as illustrated in FIG. 4 for the conversion of a compound of formula 14 to a compound of formula 15.

Figure 7:
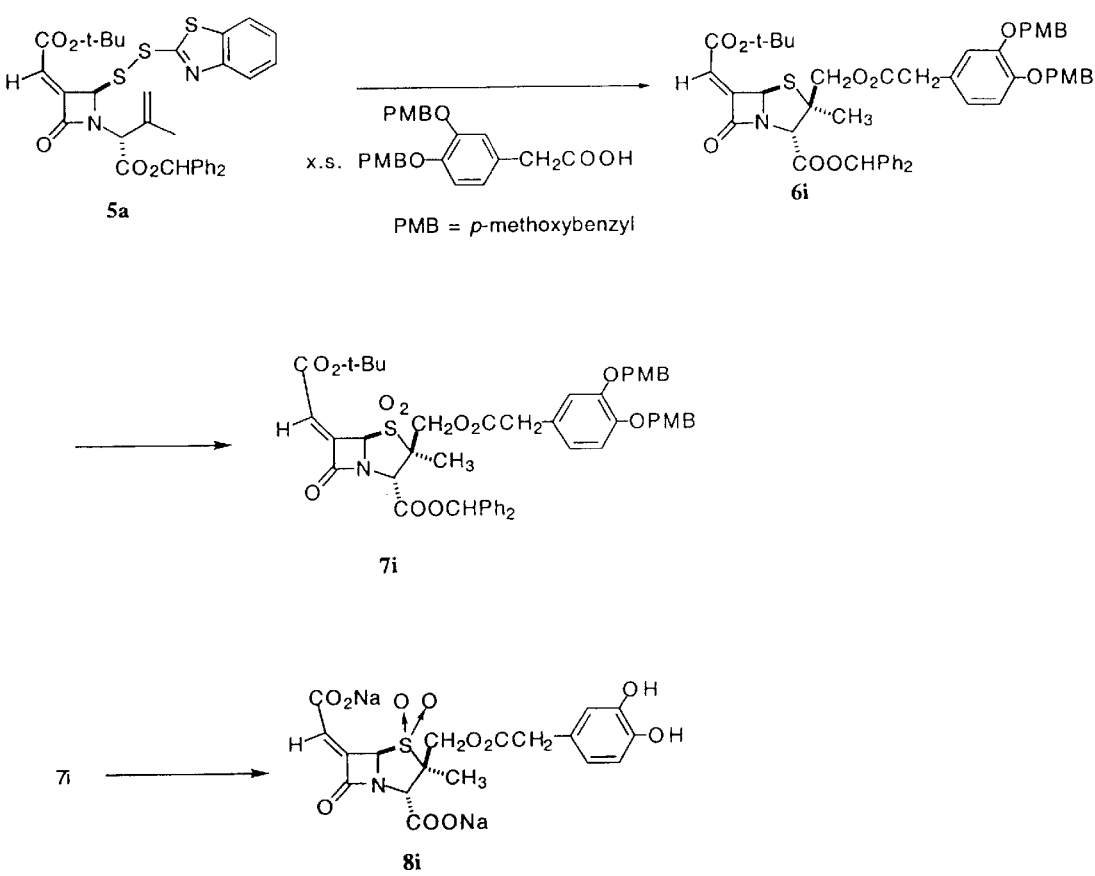
FIG. 7 illustrates the preparation of compounds of the invention (6$i$, 7$i$, and 8$i$).

As illustrated in FIG. 7, compound 6*i* can be prepared from compound 5*a* by treatment with 3,4-di-(4-methoxybenzyloxy)phenylacetic acid and silver acetate under conditions similar to those described in Example 6. Oxidation with mCPBA under conditions similar to those described in Example 12 gives a sulfoxide of formula 7*i*. Deprotection of compound 7*i* under standard conditions (e.g. similar to those described in Example 21) gives the diacid of formula (I), which can be converted to the disalt of formula 8*i* by treatment with a suitable base (e.g. sodium bicarbonate) under standard conditions.

Figure 8:
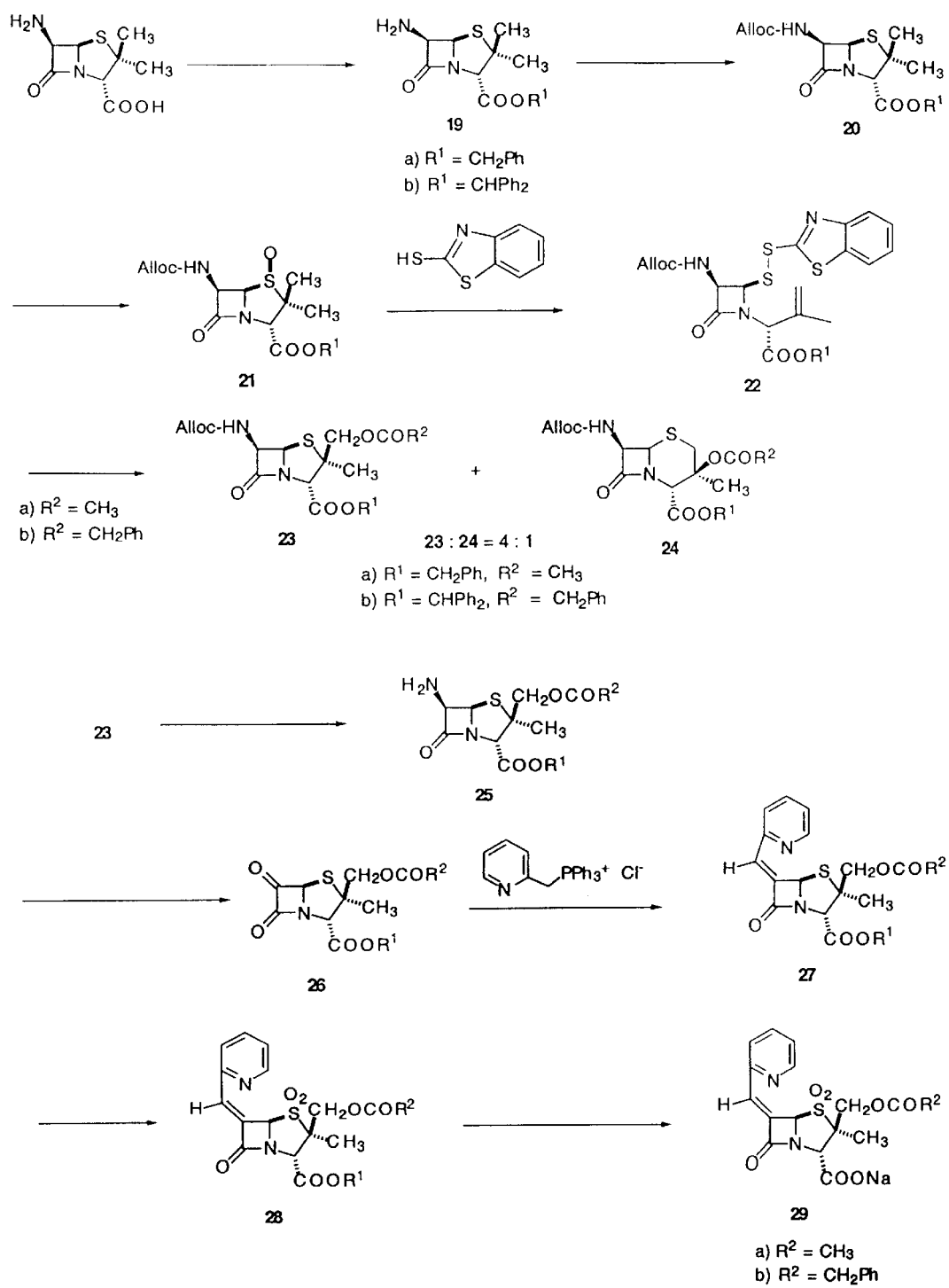
FIG. 8 illustrates the preparation of compounds of the invention (29$a$ and 29$b$).

As illustrated in FIG. 8, a compound of formula 29*a* or 29*b* can be prepared from 6-Aminopenicillinic acid (6-APA) by formation of the benzyl or benzhydryl ester, to give a compound of formula 19*a* or 19*b*. Reaction with allyl chloroformate gives the N-allyloxycarbonyl derivative 20*a* or 20*b*. Oxidation of the sulfide to the sulfoxide gives compounds 21*a* and 21*b*, which can be heated with mercaptobenzothiazole to produce the ring opened disulfides 22*a* and 22*b*. Compound 22*a* was then treated with an excess of acetic acid in the presence of 2 eq of AgOAc to produce a 4:1 mixture of the 2β-substituted penam 23*a* and the cepham 24*a*. Likewise compound 22*b* was treated with an excess of phenylacetic acid in the presence of 2 eq of AgOAc to produce a 4:1 mixture of the 2β-substituted penam 23*b* and the corresponding cepham 24*b*, respectively. These mixtures were separated to give the purified penams 23*a* and 23*b*, which were deprotected at nitrogen by reaction with (n-Bu)$_3$SnH in the presence of a catalytic amount of Pd(PPh$_3$)$_4$ to give amines, 25*a* and 25*b*. Treatment with isopropyl nitrite gives the corresponding diazocompounds, which were immediately converted to the corresponding ketones by reaction with excess propylene oxide in the presence of a catalytic amount of Rh$_2$OAc$_4$. The ketones were derivatized by reaction with the Wittig reagent [(2-pyridyl)methylene]triphenylphosporane to produce alkenes 27*a* and 27*b*, which were oxidized with excess MCPBA to produce sulfones 28*a* and 28*b*. Sulfone 28*a* was deprotected by reaction with LiI in refluxing EtOAc to produce sodium salt 29*a*. Sulfone 28*b* was deprotected by reaction with trifluoroacetic acid in anisole, and subsequent treatment with sodium bicarbonate, to produce sodium salt 29*b*.

Figure 5:
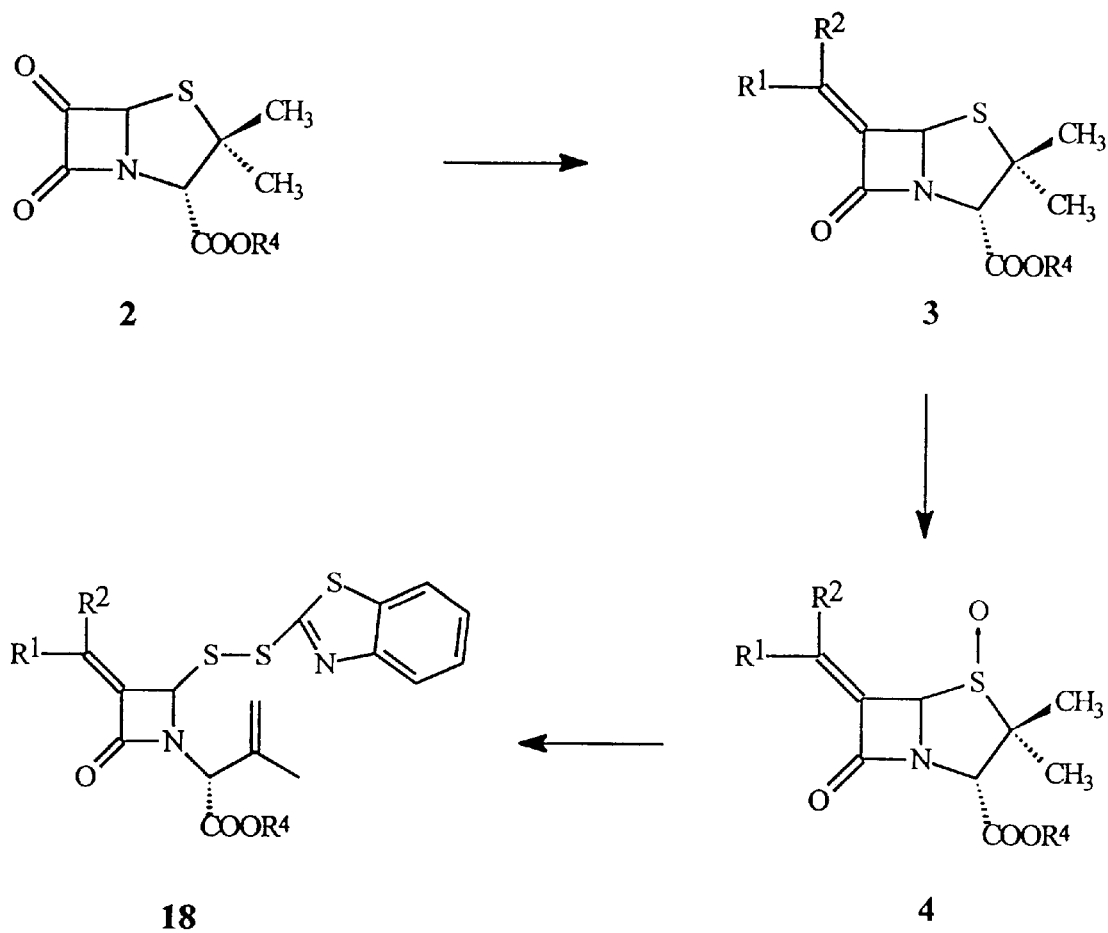
FIG. 5 illustrates the synthesis of an intermediate of formula (18) that is useful for preparing compounds of the invention.

A useful intermediate for the preparation of a compound of the invention is a compound of formula 18. As illustrated in FIG. 5, a compound of formula 18 can be prepared by treatment of 6-oxopenicillinate 2 (Hagiwara, D. F.; Sawada, K.; Ohnami, T.; Aratani, M.; Hashimoto, M., *J. Chem. Soc. Chem. Commun.*, 578 (1982)) with a compound of formula R$^1$ R$^2$C=PPh$_3$ to give a 6-alkylidene penicillinate of formula 3. Reaction of a compound of formula 3 with 1 equivalent of mCPBA in CH$_2$Cl$_2$ gives a sulfoxide of formula 4, which can be heated to reflux in toluene in the presence of 2-mercaptobenzothiazole to obtain the disulfide of formula (18).

Another useful intermediate for the preparation of a compound of the invention is an ylide, for example a ylide of formula R$^1$ R$^2$C=PPh$_3$. Ylides can be prepared using techniques that are well known in the art, for example techniques such as those described in Jerry March "Advanced Organic Chemistry" John Wiley & Sons, 4 ed. 1992, 956–963. Suitable ylides are also disclosed in U.S. Pat. No. 5,597,817, issued Jan. 29, 1997; and U.S. Pat. No. 5,629,306, issued May 13, 1997.

It is noted that many of the starting materials employed in the synthetic methods described above are commercially available or are reported in the scientific literature. It is also noted that it may be desirable to optionally use a protecting group during all or portions of the above described synthetic procedures. Such protecting groups and methods for their introduction and removal are well known in the art (see Greene, T. W.; Wutz, P. G. M. "Protecting Groups In Organic Synthesis" second edition, 1991, New York, John Wiley & sons, Inc.).

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example, calcium) salts of carboxylic acids can also be made.

Prefered salts of the invention include disalts prepared from acids of formula (I) wherein R$^1$ or R$^2$ is carboxy and R$^4$ is hydrogen. Prefered salts also include monosalts (e.g. a sodium salt) prepared from an acid of formula (I) wherein R$^4$ is hydrogen. The invention also provides a method for preparing a compound of the invention comprising forming a mono-, di-, or tri-salt from a coresponding compound of formula (I).

The compounds of formula I can be formulated as pharmaceutical compositions and administered to a mammalian host, such as a human patient in a variety of forms adapted to a selected route of administration, i.e., by oral, parenteral, intravenous, intramuscular, topical, or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1 –5 wt-%, preferably about 0.5–2.5 wt-%. Single dosages for injection, infusion or ingestion will generally vary between 50–1500 mg, and may be administered, i.e., 1–3 times daily, to yield levels of about 0.5–50 mg/kg, for adults.

Accordingly, the invention provides a pharmaceutical composition, comprising an effective amount of a compound of formula I as described hereinabove; or a pharmaceutically acceptable salt thereof; and a pharmaceutically acceptable carrier. The invention also provides a pharmaceutical composition comprising an effective amount of a compound of formula I, as described hereinabove; or a pharmaceutically acceptable salt thereof; a β-lactam antibiotic; and a pharmaceutically acceptable carrier. Any β-Lactam antibiotic is suitable for use in the pharmaceutical composition of the invention. β-Lactam antibiotics which are well known in the art include those disclosed by R. B. Morin and M. Gorin, M.Eds.; Academic Press, New York, 1982; vol. 1–3. Preferred β-Lactam antibiotics, suitable for use in the pharmaceutical composition of the invention, include β-lactam antibiotics which are preferentially deactivated by Class A and Class C β-lactamase enzymes, for example, amoxicillin, piperacillin, ampicillin, ceftizoxime, cefotaxime, cefuroxime, cephalexin, cefaclor, cephaloridine, and ceftazidime.

The ability of a compound of the invention to function as a β-lactamase inhibitor can be demonstrated using the test described below, or using other tests which are well known in the art.

Figure 6:
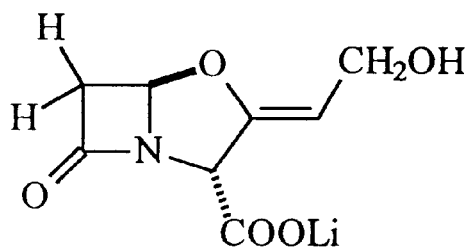
FIG. 6 shows the structure of the β-lactamase inhibitors clavulanic acid, tazobactam and the compound of formula 9.
Figure 6:
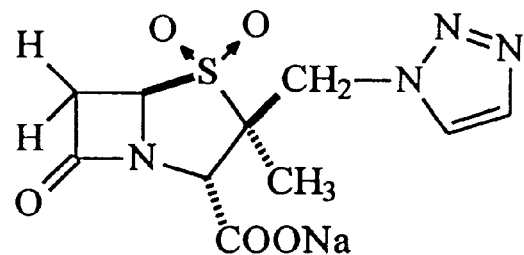
Figure 6:
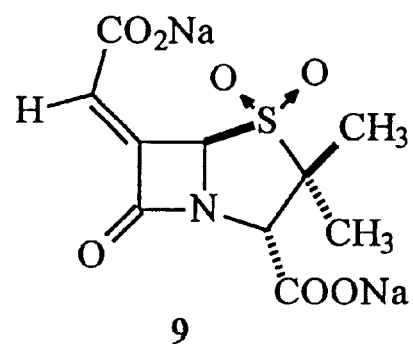

Representative compounds of the invention, as well as the known commercial inhibitors clavulanic acid and tazobactam, and the previously reported 2β-methyl compound 9 (Buynak et al., *Bioorg. Med. Chem. Lett.*, 5, 1513 (1995)) (see FIG. 6 for structures) were evaluated as inhibitors of the β-lactamase of *Enterobacter cloacae* P99 and TEM-1. The $IC_{50}$ value of each compound was determined as follows. Following a 10 minute incubation of a dilute solution of enzyme (2.56 nM) and inhibitor (<0.64 μM), a 50 μL aliquot of the incubation mixture was further diluted into 1 mL nitrocefin (a substrate) solution, and the rate of hydrolysis was measured during a 1 minute period by monitoring the absorbance of nitrocefin as a function of time.

The results are summarized in Table 1. The β-lactamase inhibiting activity of compound 8a, 8b, 8d, and 8g is greater than the activity of compound 9 by at least a factor of 10 for TEM-1; and the β-lactamase inhibiting activity of compound 8a and 8c is greater than the activity of compound 9 by a factor of nearly 2 for P99. Compounds 8a, 8b, 8d, and 8g are also more active than the current commercial inhibitors clavulanic acid and tazobactam. In addition, compounds 29a and 29b demonstrate potent β-lactamase inhibiting activity against TEM-1 and P99.

TABLE 1

β-Lactamase Inhibitory Activity

| Compounds | $IC_{50}(\mu M)$ Ent. cloacae P99 | $IC_{50}(\mu M)$ TEM-1 |
|---|---|---|
| tazobactam | 17.2 | 0.32 |
| clavulanic acid | >20000 | 60 |
| 8a | 0.383 | 0.213 |
| 8b | NT | 0.19 |
| 8c | 0.30 | 1.84 |
| 8d | 0.54 | 0.015 |
| 8e | 2.66 | 2.72 |
| 8g | 0.64 | 0.23 |
| 8h | 3.69 | 2.37 |
| 8i | 0.37 | 0.105 |
| 9 | 0.75 | 2.51 |
| 12a | 7.62 | 39.0 |
| 12b | 6.96 | 44.5 |
| 12c | 105.4 | 120.5 |
| 17 | 6.76 | 21.62 |
| 29a | 0.062 | 0.004 |
| 29b | NT | 0.39 |

Compounds of the invention have been shown to possess activity as β-lactamase inhibitors. Accordingly, the invention provides a method comprising inhibiting a β-lactamase by contacting said β-lactamase with an effective amount of a compound of formula I; or a pharmaceutically acceptable salt thereof. The β-lactamase may be contacted with the compound of claim in vitro or in vivo.

The invention also provides a therapeutic method comprising inhibiting a β-lactamase in a mammal (preferably a human) in need of such therapy, by administering an effective inhibitory amount of a compound of formula I; or a pharmaceutically acceptable salt thereof.

Because compounds of the invention inhibit β-lactamase enzymes, they may also be useful to increase the effectiveness of β-lactam antibiotics which are degraded by such enzymes. Accordingly, the invention provides a method comprising enhancing (increasing by a detectable amount) the activity of a β-lactam antibiotic, by administering the β-lactam antibiotic to a mammal (preferably a human) in need thereof, in combination with an effective amount of a compound of formula I; or a pharmaceutically acceptable salt thereof.

The invention also provides a method comprising treating a β-lactam resistant bacterial infection in a mammal (preferably a human), by administering an effective amount of a β-lactam antibiotic in combination with an effective β-lactamase inhibiting amount of a compound of formula I; or a pharmaceutically acceptable salt thereof.

Additionally, the invention provides a compound of formula I for use in medical therapy (preferably for use in treating a β-lactam resistant infection), as well as the use of a compound of formula I for the manufacture of a medicament useful for reducing β-lactamase activity in a mammal.

Compounds of the invention possess specific 6-alkylidene substituents and specific 2β-substituents. This combination of structural features provides compounds that can exhibit extremely high activity as inhibitors of β-lactamase. Additionally, compounds of the invention may possess other biological or pharmacological properties which make them superior to known compounds as therapeutic agents.

The invention will now be illustrated by the following non-limiting examples.

EXAMPLE 1

Benzhydryl 2β-(acetoxymethyl)-6-[(Z)-(t-butoxycarbonyl)methylene]penicillinate (6a)

To a solution of a compound of formula 5a (0.70 g, 1.086 mmol) in $CH_2Cl_2$ were added AcOH (2.78 g, 46.68 mmol) and AgOAc (0.376 g, 2.26 mmol) and the reaction was stirred for 4 hours. The reaction mixture was then filtered through a celite bed and the filtrate was washed with a saturated $NaHCO_3$ solution. The organic layer was dried ($Na_2SO_4$), concentrated, and purified by flash column chromatography to yield the title compound 6a (390 mg, 66.8%). $^1H$ NMR ($CDCl_3$): δ 7.39–7.26 (10H, m), 6.95 (1H, s), 6.18 (1H, s), 6.01 (1H, s), 4.95 (1H, s), 4.12 (1H, d), 3.77 (1H, d), 2.09 (3H, s), 1.51 (9H, s), 1.24 (3H, s).

The intermediate of formula 5a was prepared as follows.

a. Benzhydryl 6-[(Z)-t-butoxycarbonylmethylene]penicillinate (3a).

To a solution of (3.6 g, 9.4 mmol) benzhydryl 6-oxopenicillinate, compound 2, (J. D. Buynak et al., *J. Org. Chem.*, 58, 1325–1335 (1993)) in 50 mL anhydrous $CH_2Cl_2$ at −78° C., was added a solution of (tert-butoxycarbonylmethylene) triphenylphosphorane (3.6 g, 9.56 mmol) in an additional 50 mL anhydrous $CH_2Cl_2$. The reaction was allowed to stir for 80 minutes at −78° C., then poured into a separatory funnel containing 400 mL cold saturated aqueous $NH_4Cl$. The layers were separated and the aqueous layer was extracted a second time with 50 mL $CH_2Cl_2$. The combined organic layers were dried ($Na_2SO_4$) and concentrated. The resulting material was further purified by column chromatography ($SiO_2$, $CH_2Cl_2$) to yield a white foam (2.38 g, 53% yield). $^1H$ NMR ($CDCl_3$): δ 7.40–7.27 (10H, m), 6.93 (1H, s), 6.17 (1H, d, J=4 Hz), 5.97 (1H, d, J=4 Hz), 4.63 (1H, s), 1.54 (3H, s), 1.49 (9H, s), 1.25 (3H, s).

b. Benzhydryl 6-[(Z)-t-butoxycarbonyl)methylene]penicillinate sulfoxide (4a).

To a solution of benzhydryl 6-[(Z)-(t-butoxycarbonyl)methylene] penicillinate, compound 3a, (4.5 g, 9.349 mmol) in $CH_2Cl_2$ was added mCPBA (2.32 g, 9.394 mmol) in one portion and the reaction mixture was stirred for 1 hour at room temperature. The reaction mixture was washed with $NaHCO_3$ solution, dried over $Na_2SO_4$, concentrated and purified by column chromatography to give 5:1 mixtures of β:α sulfoxides (2.93 g, 63%). $^1H$ NMR ($CDCl_3$) of β-sulfoxide: δ 7.37–7.31 (10H, m), 7.00 (1H, s), 6.50 (1H, s), 5.67 (1H, s), 4.77 (1H, s), 1.67 (3H, s), 1.52 (9H, s), 0.98 (3H, s). $^1H$ NMR of α-sulfoxide: δ 7.37–7.31 (10H, m), 7.00 (1H, s), 6.02 (1H, s), 5.33 (1H, s), 4.79 (1H, s), 1.68 (3H, s), 1.51 (9H, s), 0.96 (3H, s).

c. 4-(2'-Benzothiazolyldithio)-3-[(Z)-(t-butoxycarbonyl)methylene]-1-[1'-diphenylmethyloxycarbonyl-2'-methylprop-2'-enyl]azetidin-2-one (5a).

To a solution of benzhydryl 6-[(Z)-(t-butoxycarbonyl)methylene] penicillinate sulfoxide, compound 4, (2.35 g, 4.74 mmol) in toluene, was added 2-mercaptobenzothiazole (0.792 g, 4.74 mmol) and the reaction was heated to reflux for 4.5 hours. Volatiles were removed under reduced pressure to give compound 5a (3.15 g, 100%). $^1$H NMR (CDCl$_3$): δ 7.86 (1H, d, J=8 Hz), 7.71 (1H, d, J=8 Hz), 7.42–7.25 (12H, m), 6.88 (1H, s), 6.09 (1H, s), 5.96 (1H, s), 5.14 (1H, s), 5.12 (1H, s), 5.00 (1H, s), 1.88 (3H, s), 1.49 (9H, s).

EXAMPLE 2

Benzhydryl 2β-(chloroacetoxymethyl)-6-[(Z)-(t-butoxycarbonyl)methylene]penicillinate (6b)

A solution of 5a (2.3 g, 3.57 mmol), chloroacetic acid (14.4 g, 153 mmol) and AgOAc (1.24 g, 7.4 mmol) in CH$_2$Cl$_2$ (100 mL) was stirred for 5 hours at room temperature. The reaction mixture was filtered and filtrate was washed with saturated NaHCO$_3$ (2×100 mL). The organic layer was dried (Na$_2$SO$_4$), concentrated, and purified by column chromatography (4:1 CH$_2$Cl$_2$: hexane as eluent) to give the title compound; 1.4 g (69%); $^1$H NMR (CDCl$_3$): δ 7.39–7.30 (m, 10H), 6.95 (s, 1H), 6.19 (s, 1H), 6.02 (s, 1H), 4.93 (s, 1H), 4.24 (d, J=11.6 Hz, 1H), 4.13 (d, J=14.8 Hz, 1H), 4.07 (d, J=14.8 Hz), 1H), 3.85 (d, J=11.6 Hz, 1H), 1.51 (s, 9H), 1.26 (s, 3H).

EXAMPLE 3

Benzhydryl 2β-(formyloxymethyl)-6-[(Z)-(t-butoxycarbonyl)methylene]penicillinate (6c)

A solution of 5a (1.5 g, 2.33 mmol), 97% formic acid (4.02 mL, 101.3 mmol) and AgOAc (0.81 g, 4.84 mmol) in CH$_2$Cl$_2$ (45 mL) was stirred for 5 hours at room temperature. The reaction mixture was filtered and the filtrate was washed with saturated aqueous NaHCO$_3$ (2×50 mL). The organic layer was dried (Na$_2$SO$_4$) and concentrated to yield a crude formate (1.05 g, 86%) which was directly oxidized to the sulfone.

EXAMPLE 4

Benzhydryl 2β-(phenylacetoxymethyl)-6-[(Z)-(t-butoxycarbonyl)methylene]penicillinate (6d)

A mixture of disulfide 5a (2.0 g, 3.31 mmol), phenylacetic acid (19.4g, 142.4 mmol) and AgOAc (1.15 g, 6.88 mmol) in CH$_2$Cl$_2$ (80 mL) was stirred for 5 hours at room temperature. The reaction mixture was filtered through celite and washed with aq NaHCO$_3$ solution (2×100 mL). The organic layer was dried (Na$_2$SO$_4$), concentrated, and purified by column chromatography to give the title compound 6d; 1.04 g, 51%; $^1$H NMR (CDCl$_3$): δ 7.37–7.23 (m, 15H), 6.94 (s, 1H), 6.16 (s, 1H), 5.99 (s, 1H), 4.91 (s, 1H), 4.14 (d, J=11.9 Hz, 1H), 3.78 (d, J=11.9 Hz, 1H), 3.67 (ABq, 2H), 1.51 (s, 9H), 1.15 (s, 3H).

EXAMPLE 5

Benzhydryl 2β-(acetoxymethyl)-6-[(Z)-(methoxycarbonyl)methylene]penicillinate (6e)

A mixture of disulfide 5b (350 mg, 0.581 mmol), acetic acid (1.44 mL, 25.27 mmol) and AgOAc (0.201 g, 1.21 mmol) in CH$_2$Cl$_2$ (15 mL) was stirred for 5 hours at room temperature. The reaction mixture was filtered through celite and washed with aq NaHCO$_3$ solution (2×20 mL). The organic layer was dried (Na$_2$SO$_4$), concentrated, and purified by column chromatography to give the title compound 6e; (190 mg, 75%; $^1$H NMR (CDCl$_3$): δ 7.32–7.18 (m, 10H), 6.89 (s, 1H), 6.22 (s, 1H), 5.99 (s, 1H), 4.86 (s, 1H), 4.03 (d, J=11.8 Hz, 1H), 3.74–3.72 (m, 4H), 2.01 (s, 3H), 1.15 (s, 3H).

The intermediate disulfide 5b was prepared as follows.
a. Benzhydryl 6-[(Z)-(methoxycarbonyl)methylene] penicillinate (3b).

To a solution of ketone 2 (2.0 g, 5.25 mmol), in anhydrous THF (20 mL) at −78° C. was added methyl (triphenylphosphoranylidene)acetate (1.75 g, 5.25 mmol) in THF (20 mL) and the reaction mixture stirred at −78° C. for 45 min. The reaction mixture was poured onto saturated aqueous NH4Cl (50 mL) and extracted with dichloromethane (60 mL). The organic layer was dried (Na$_2$SO$_4$), concentrated, and purified on silica gel chromatography to produce 3b (1.35 g, 59%). $^1$H NMR (CDCl$_3$): δ 7.37–7.30 (10H, m), 6.96 (1H, s), 6.30 (1H, s), 6.03 (1H, d, s), 4.66 (1H, s), 3.81 (3H, s), 1.56 (3H, s), 1.27 (3H, s).

b. Benzhydryl 6-[(Z)-(methoxycarbonyl)methylene] penicillinate sulfoxide (4b).

To a solution of sulfide 3b (1.2 g, 2.75 mmol) in CH$_2$Cl$_2$ (20 mL) was added 70% mCPBA (0.68 g, 2.75 mmol) and the reaction mixture was stirred for 30 minutes at room temperature. The reaction mixture was then poured into saturated aqueous NaHCO$_3$ (30 mL), the organic layer separated, dried (Na$_2$SO$_4$), concentrated, and purified by column chromatography to produce 4b (1.10 g, 88%). $^1$H NMR of α-sulfoxide: δ 7.37–7.30 (10H, m), 7.00 (1H, s), 6.59 (1H, s), 5.69 (1H, s), 4.78 (1H, s), 3.83 (s, 3H), 1.67 (3H, s), 0.98 (3H, s).

C. 4-(2'-Benzothiazolyldithio)-3-[(Z)-(methoxycarbonyl)methylene]-1-[1'-(diphenylmethyloxycarbonyl)-2'-methylprop-2'-enyl]azetidin-2-one (5b).

A mixture of sulfoxide 4b (1.1 g, 2.43 mmol) and 2-mercaptobenzothiazole (0.405 g, 2.43 mmol) in toluene (35 mL) was heated to reflux for 4 hours. Volatiles were removed under vacuum to produce disulfide 5b (1.46 g, 100%). $^1$H NMR (CDCl$_3$): δ 7.78 (1H, d, J=8.0 Hz), 7.62 (1H, d, J=8.0 Hz), 7.35–7.06 (12H, m), 6.81 (1H, s), 6.09 (1H, s), 5.93 (1H, s), 5.06 (1H, s), 5.05 (1H, s), 4.89 (1H, s), 3.60 (3H, s), 1.8 (3H, s).

EXAMPLE 6

Benzhydryl 2p-(chloroacetoxymethyl)-6-[(Z)-(methoxycarbonyl)methylene]penicillinate (6f)

A mixture of disulfide 5b (2.0 g, 3.32 mmol), chloroacetic acid (13.42 g, 142.82 mmol) and AgOAc (1.15 g, 6.91 mmol) in CH$_2$Cl$_2$ (60 mL) was stirred for 5 hours at room temperature. The reaction mixture was filtered through celite and washed with aq NaHCO$_3$ solution (2×100 mL). The organic layer was dried (Na$_2$SO$_4$), concentrated, and purified by column chromatography to give the title compound 6f; 1.2 g, 77%; $^1$H NMR (CDCl$_3$): δ 7.38–7.29 (m, 10H), 6.96 (s, 1H), 6.31 (s, 1H), 6.07 (s, 1H), 4.94 (s, 1H), 4.20 (d, J=12.3 Hz, 1H), 4.11 (d, J=16.8 Hz, 1H), 4.08 (d, J=16.8 Hz, 1H), 3.85 (d, J=12.3 Hz, 1H), 3.81 (s, 3H), 1.24 (s, 3H).

EXAMPLE 7

Benzhydryl 2β-(acetoxymethyl)-6-[(Z)-(t-butoxycarbonyl)methylene]penicillinate-1,1-dioxide (7a)

To a solution of benzhydryl 2β-(acetoxymethyl)-6-[(Z)-(tert-butoxycarbonyl)methylene]penicillinate (290 mg, 0.54 mmol, 6a) in CH$_2$Cl$_2$ (10 mL) and pH 6.4 phosphate buffer solution (10 mL) was added mCPBA (293 mg, 1.18 mmol). The mixture was stirred at room temperature for 18 hours, and then diluted with CH$_2$Cl$_2$ (10 mL). The organic layer was washed with NaHCO$_3$ solution (25 mL), dried (Na$_2$SO$_4$), concentrated and purified by column chromatography to give the title compound; 226 mg, 73%; $^1$H NMR (CDCl$_3$): δ 7.37–7.33 (10H, m), 6.97 (1H, s), 6.49 (1H, s), 5.47 (1H, s), 4.85 (1H, s), 4.51 d, J=), 4.35 (1H, d, J=), 2.08 (3H, s), 1.54 (9H, s), 1.18 (3H, s); IR (CHCl$_3$): 1799, 1751.7; $^{13}$C NMR (CDCl$_3$): δ 169.76, 165.55, 165.03, 161.94, 143.99, 138.65, 138.52, 128.87, 128.76, 128.54, 127.56, 127.13, 127.18, 84.09, 79.67, 72.67, 65.63, 64.17, 60.90, 27.89, 20.56, 15.57.

EXAMPLE 8

Benzhydryl 2β-(chloroacetoxymethyl)-6-[(Z)-(t-butoxycarbonyl)methylene]penicillinate 1,1-dioxide (7b)

To a solution of sulfide 6b (1.29 g, 2.1 mmol) in CH$_2$Cl$_2$ (30 mL) was added mCPBA (70%, 0.8 g, 4.62 mmol) in one portion followed by pH 6.4 phosphate buffer solution (30 mL) and the reaction mixture was stirred overnight. The organic layer was separated, washed with saturated aqueous NaHCO$_3$ (1×50 mL), dried (Na$_2$SO$_4$), concentrated and purified by silica gel chromatography (CH$_2$Cl$_2$ as eluent) to give the title compound 7b; 0.893 g, 70.5%; $^1$H NMR (CDCl$_3$): δ 7.39–7.30 (10H, m), 6.99 (1H, s), 6.53 (1H, s), 5.50 (s, 1H), 4.86 (s, 1H), 4.61 (d, J=12.19 Hz, 1H), 4.47 (d, J=12.19 Hz, 1H), 4.12 (d, J=15.18 Hz, 1H), 4.06 (d, J=15.18 Hz, 1H), 1.54 (s, 9H), 1.27 (s, 3H).

EXAMPLE 9

Benzhydryl 2β-(formyloxymethyl)-6-[(Z)-(t-butoxycarbonyl)methylene]-penicillinate 1,1-dioxide (7c)

The crude formate 6c (1.05 g, 2.01 mmol) was dissolved in CH$_2$Cl$_2$ (25 mL) and mCPBA (70%, 1.385 g, 8.03 mmol) and pH 6.4 phosphate buffer (25 mL) was added. The reaction mixture was stirred at room temperature for 14 hours. The organic layer was separated, washed with aqueous saturated NaHCO$_3$ (50 mL), dried (Na$_2$SO$_4$), concentrated and purified by silica gel chromatography to give the title compound 7c; 0.76 g, 68%; $^1$H NMR (CDCl$_3$): δ 7.42–7.28 (m, 10H), 6.98 (s, 1H), 6.52 (s, 1H), 5.48 (s, 1H), 4.81 (s, 1H), 4.59 (d, J=12.16 Hz, 1H), 4.49 (d, J=12.16 Hz, 1H), 1.51 (s, 9H), 1.21 (s, 3H).

EXAMPLE 10

Benzhydryl 2β-(phenylacetoxymethyl)-6-[(Z)-(1-butoxycarbonyl)methylene]penicillinate 1,1-dioxide (7d)

To a solution of sulfide 6d (0.65 g, 1.06 mmol) in CH$_2$Cl$_2$ (20 mL) was added mCPBA (70%, 0.58 g, 2.33 mmol) in one portion followed by pH 6.4 phosphate buffer solution (20 mL) and the reaction mixture was stirred overnight. The organic layer was separated, washed with saturated aqueous NaHCO$_3$ (1×20 mL), dried (Na$_2$SO$_4$), concentrated and purified by silica gel chromatography to give the title compound 7d; 0.490 g, 71.6%; $^1$H NMR (CDCl$_3$): δ 7.37–7.26 (15H, m), 6.95 (1H, s), 6.47 (1H, s), 5.46 (s, 1H), 4.80 (s, 1H), 4.54 (d, J=12.3 Hz, 1H), 4.36 (d, J=12.3 Hz, 1H), 3.65 (s, 2H), 1.53 (s, 9H), 1.09 (s, 3H).

EXAMPLE 11

Benzhydryl 2β-(acetoxymethyl)-6-[(Z)-(methoxycarbonyl)methylene]-penicillinate 1,1-dioxide (7e)

To a solution of benzhydryl 2β-(acetoxymethyl)-6-[(Z)-(methoxycarbonyl)-methylene]penicillinate (6e, 190 mg, 0.43 mmol) in CH$_2$Cl$_2$ (10 mL) and pH 6.4 phosphate buffer solution (10 mL) was added mCPBA (225 mg, 0.913 mmol). The mixture was stirred at room temperature for 18 hours, and then diluted with CH$_2$Cl$_2$ (10 mL). The organic layer was washed with NaHCO$_3$ solution (25 mL), dried (Na$_2$SO$_4$), concentrated and purified by column chromatography to give the title compound 7e; 140 mg, 68.9%, $^1$H NMR (CDCl$_3$): δ 7.39–7.23 (10 1l, m), 6.98 (1H, s), 6.59 (1H, s), 5.46 (1H, s), 4.82 (1H, s), 4.57 (1H, d, J=12.2 Hz), 4.37 (1H, d, J=12.2 Hz), 3.86 (s, 3H), 2.02 (3H, s), 1.19 (3H, s).

EXAMPLE 12

Benzhydryl 2β-(chloroacetoxymethyl)-6-[(Z)-(methoxycarbonyl)methylene]penicillinate 1,1-dioxide (7f)

To a solution of benzhydryl 2β-(chloroacetoxymethyl)-6-[(Z)-(methoxycarbonyl)methylene]penicillinate (6f, 1.2 g, 2.55 mmol) in CH$_2$Cl$_2$ (20 mL) and pH 6.4 phosphate buffer solution (20 mL) was added mCPBA (70%, 1.38 g, 5.61 mmol). The mixture was stirred at room temperature for 18 hours, and then diluted with CH$_2$Cl$_2$ (20 mL). The organic layer was washed with NaHCO$_3$ solution (50 mL), dried (Na$_2$SO$_4$), concentrated and purified by column chromatography to give the title compound 7f; 920 mg, 72%; $^1$H NMR (CDCl$_3$): δ 7.39–7.28 (10H, m), 6.99 (1H, s), 6.61 (1H, s), 5.47 (1H, s), 4.82 (1H, s), 4.67 (1H, d, J=12.2 Hz), 4.49 (1H, d, J=12.2 Hz), 4.07 (ABq, 2H), 3.85 (s, 3H), 1.20 (3H, s).

EXAMPLE 13

Benzhydryl 2β-[[(1-methyl-1H-tetrazol-5-yl)thio]acetoxymethyl]-6-[(Z)-(-butoxycarbonyl)methylene]penicillinate 1,1-dioxide (7g)

A mixture of chloride 7b (0.40 g, 0.663 mmol), 5-mercapto-1-methyl-1H-tetrazole (93 mg, 0.796 mmol) and NaHCO$_3$ (67 mg, 0.796 mmol) in acetone-water (8 mL, 3:1) was stirred for 6 hours at room temperature. The reaction mixture was diluted with CH$_2$Cl$_2$ (50 mL), washed with 5% NaHCO$_3$ solution (50 mL). The organic layer was dried, concentrated and purified by column chromatography (5% EtOAc/CH$_2$Cl$_2$ as eluent) to give the title compound 7g; 0.29 g, 64%; $^1$H NMR (CDCl$_3$): δ 7.37–7.32 (m, 10H), 6.97 (s, 1H), 6.52 (s, 1H), 5.54 (s, 1H), 4.83 (s, 1H), 4.61 (d, J=12.14 Hz, 1H), 4.44 (d, J=12.14 Hz, 1H), 4.21 (d, J=15.67 Hz, 1H), 4.11 (d, J=12.67 Hz, 1H), 3.95 (s, 3H), 1.53 (s, 9H), 1.24 (s, 3).

EXAMPLE 14

Benzhydryl 2β-[[(1-methyl-1H-tetrazol-5-yl)thio]acetoxymethyl]-6-[(Z)-(methoxycarbonyl)methylene]penicillinate 1,1-dioxide (7h)

A mixture of chloride 7f (200 mg, 0.397 mmol), 5-mercapto-1-methyl-1H-tetrazole (55 mg, 0.477 mmol) and NaHCO$_3$ (40 mg, 0.477 mmol) in acetone-water (4 mL, 3:1) was stirred for 6 hours at room temperature. The reaction mixture was diluted with CH$_2$Cl$_2$ (30 mL), washed with 5% NaHCO$_3$ solution (30 mL). The organic layer was dried, concentrated and purified by column chromatography (5% EtOAc/CH$_2$Cl$_2$ as eluent) to give the title compound 7h; 0.178 g, 77%; $^1$H NMR (CDCl$_3$): δ 7.36–7.33 (m, 10H), 6.97 (s, 1H), 6.61 (s, 1H), 5.44 (s, 1H), 4.81 (s, 1H), 4.66 (d, J=12.12 Hz, 1H), 4.48 (d, J=12.12 Hz, 1H), 4.19 (d, J=16.81 Hz, 1H), 4.09 (d, J=16.81 Hz, 1H), 4.03 (s, 3H), 3.89 (s, 3H), 1.25 (s, 3H).

EXAMPLE 15

Disodium salt of 2β-(acetoxymethyl)-6-[(Z)-carboxymethylene]-penicillinic acid-1,1-dioxide (8a)

To a solution of benzhydryl 2β-(acetoxymethyl)-6-[(Z)-(tert-butoxycarbonyl)methylene]penicillinate-1,1-dioxide, (300 mg, 0.526 mmol, 7a) in anisole (1.7 mL, 15.8 mmol) at 0° C. was added trifluoroacetic acid (4.86 mL, 63.26 mmol) over 5 minutes under argon. The reaction mixture was stirred for 20 minutes at 0° C. and for 2 minutes at 30° C. Excess TFA was removed in vacuo. The residue was again dissolved in EtOAc (10 mL) and treated with aqueous NaHCO$_3$ (44 mg in 5 mL) and aqueous layer was purified by reverse phrase chromatography (deionized water as eluent) to give the title compound 8a; 160 mg, 77.6%; $^1$H NMR (D$_2$O): δ 6.53 (1H, s), 5.62 (1H, s), 4.52 (1H, d, J=), 4.38 (1H, s), 4.36 (1H, d, J=), 1.98 (3H, s), 1.41 (3H, s).

EXAMPLE 16

Disodium salt of 2β-(chloroacetoxymethyl)-6-[(Z)-carboxymethylene]-penicillinate 1,1-dioxide (8b)

Sulfone 7b (190 mg, 0.315 mmol) was dissolved in anisole (1.03 mL, 9.45 mmol) and cooled in an ice bath. To this solution was added trifluoroacetic acid (2.92 mL, 37.84 mmol) and stirring continued for 30 minutes at 0° C. Volatiles were removed in vacuo, the residue dissolved in EtOAc (20 mL) and the solution extracted with NaHCO$_3$ solution (53 mg in 15 mL of H$_2$O). This solution was then placed on a column of CHP20P (Mitsubishi Chemical Corporation) and the disalt 8b eluted with deionized water; 60 mg, 45%; $^1$H NMR (D$_2$O): δ 6.58 (s, 1H), 5.67 (s, 1H), 4.69 (d, J=12.36 Hz, 1H), 4.54 (d, J=12.36 Hz, 1H), 4.45 (s, 1H), 4.23 (s, 2H), 1.47 (s, 3H).

EXAMPLE 17

Disodium salt of 2β-(formyloxymethyl)-6-[(Z)-carboxymethylene]-penicillinate 1,1-dioxide (8c)

Sulfone 7c (310 mg, 0.558 mmol) was dissolved in anisole (1.82 mL, 16.75 mmol) and cooled in an ice bath. To this solution was added trifluoroacetic acid (5.16 mL, 67.02 mmol) and stirring continued for 30 minutes at 0° C. Volatiles were removed in vacuo, the residue dissolved in EtOAc (30 mL) and the solution extracted with NaHCO$_3$ solution (94 mg NaHCO$_3$ in 20 mL of H$_2$O). This solution was then placed on a column of CHP20P (Mitsubishi Chemical Corporation) and the disalt 8c eluted with deionized water; 100 mg, 47.6%; $^1$H NMR (D$_2$O): δ 8.07 (s, 1H), 6.58 (s, 1H), 5.68 (s, 1H), 4.68 (d, J=12.31 Hz, 1H), 4.57 (d, J=12.31 Hz, 1H), 4.45 (s, 1H), 1.48 (s, 3H).

EXAMPLE 18

Disodium salt of 2β-(phenylacetoxymethyl)-6-[(Z)-carboxymethylene]-penicillinate 1,1-dioxide (8d)

Sulfone 7d (305 mg, 0.473 mmol) was dissolved in anisole (1.54 mL, 14.2 mmol) and cooled in an ice bath. To this solution was added trifluoroacetic acid (4.4 mL, 56.74 mmol) and stirring continued for 30 minutes at 0° C. Volatiles were removed in vacuo, the residue dissolved in EtOAc (20 mL) and the solution extracted with NaHCO$_3$ solution (80 mg NaHCO$_3$, 0.946 mmol in 15 mL of H$_2$O). This solution was then placed on a column of CHP20P (Mitsubishi Chemical Corporation) and the disalt 8d eluted with deionized water; 85 mg, 37.6%; $^1$H NMR (D$_2$O): δ 7.30–7.22 (m, 5H), 6.55 (s, 1H), 5.64 (s, 1H), 4.63 (d, J=12.46 Hz, 1H), 4.42 (d, J=12.46 Hz, 1H), 4.39 (s, 1H), 3.69 (s, 2H), 1.48 (s, 3H).

EXAMPLE 19

Sodium salt of 2β-(acetoxymethyl)-6-[(Z)-(methoxycarbonyl)methylene]-penicillinic acid 1,1 dioxide (8e)

To a solution of benzhydryl 2β-(acetoxymethyl)-6-[(Z)-(methoxycarbonyl)-methylene]penicillinate 1,1 dioxide, 7e, (270 mg, 0.512 mmol) in anisole (1.7 mL, 15.4 mmol) at 0° C. was added trifluoroacetic acid (4.86 mL, 61.5 mmol) over 5 minutes under argon. The reaction mixture was stirred for 15 minutes at 0° C. Excess TFA was removed in vacuo. The residue was again dissolved in EtOAc (20 mL) and treated with aqueous NaHCO$_3$ (5%, 10 mL) and aqueous layer was purified on a column of CHP20P (Mitsubishi Chemical Corporation) (deionized water as eluant) to give the title compound 8e; 100 mg, 51%; $^1$H NMR (D$_2$O): δ 6.68 (s, 1H), 5.79 (s, 1H), 4.57 (d, 1H, J=12.2 Hz), 4.52 (s, 1H), 4.41 (d, 1H, J=12.2 Hz), 3.74 (s, 3H), 2.00 (s, 3H), 1.46 (s, 3H).

EXAMPLE 20

Disodium salt of 2β-[[(1-methyl-1H-tetrazol-5-yl)thio]acetoxymethyl]-6-[(Z)-carboxymethylene] penicillinate 1,1-dioxide (8g)

Compound 7g (135 mg, 0.197 mmol) was dissolved in anisole (0.65 mL, 5.32 mmol) and cooled in an ice bath. To this solution was added trifluoroacetic acid (1.83 mL, 23.71 mmol) and stirring was continued for 30 minutes at 0° C. Volatiles were removed in vacuo and the residue dissolved in EtOAc (20 mL) and extracted with aqueous NaHCO$_3$ (33 mg dissolved in 10 mL H$_2$O). The aqueous solution was then loaded onto a column of CHP20P (Mitsubishi Chemical Corporation) and the disalt 8g eluted with deionized water; 43 mg, 43%; $^1$H NMR (D$_2$O): δ 6.57 (s, 1H), 5.61 (s, 1H), 4.63 (d, J=12.3 Hz, 1H), 4.36 (s, 1H), 3.93–3.87 (m, 5H), 1.37 (s, 3H).

EXAMPLE 21

Sodium salt of 2β-[[(1-methyl-1H-tetrazol-5-yl)thio]acetoxymethyl]-6-[(Z)-(methoxycarbonyl)methylene]penicillinate 1,1-dioxide (8h)

Compound 7h (175 mg, 0.3 mmol) was dissolved in anisole (0.98 mL, 9.0 mmol) and cooled in an ice bath. To this solution was added trifluoroacetic acid (2.77 mL, 36.02 mmol) and stirring was continued for 15 minutes at 0° C. Volatiles were removed in vacuo and the residue dissolved in EtOAc (20 mL) and extracted with aqueous 5% NaHCO$_3$ (10 mL). The aqueous solution was then loaded onto a column of CHP20P (Mitsubishi Chemical Corporation) and the salt 8h eluted with 6% EtOH/H$_2$O; 69 mg, 53%; $^1$H NMR (D$_2$O): δ 6.69 (s, 1H), 5.74 (s, 1H), 4.63 (d, J=12.2 Hz, 1H), 4.48 (d, J=12.23 Hz, 1H), 4.46 (s, 1H), 3.93 (m, 5H), 3.77 (s, 3H), 1.41 (s, 3H).

EXAMPLE 22

Benzhydryl 2-(chloromethyl)-6-[(z)-(t-butoxycarbonyl)methylene]-penicillinate (10a)

A solution of 5a (2.5 g, 3.88 mmol) and CuCl2 (0.63 g, 4.66 mmol) in $CH_2Cl_2$ (60 mL) was stirred for 7 hours at room temperature. The reaction mixture was filtered and filtrate was washed with saturated $NaHCO_3$ (100 mL). The organic layer was dried ($Na_2SO_4$), concentrated, and purified by column chromatography to give the title compound 10a; 1.43 g, 72%; $^1$H NMR (CDCl$_3$): δ 7.37–7.31 (m, 10H), 6.96 (s, 1H), 6.18 (s, 1H), 6.02 (s, 1H), 5.24 (s, 1H), 3.53 (d, J=11.8 Hz, 1H), 3.43 (d, J=11.8 Hz, 1H), 1.51 (s, 9H), 1.34 (s, 3H).

EXAMPLE 23

Benzhydryl 2β-(chloromethyl)-6-[(Z)-(methoxycarbonyl)methylene]-penicillinate (10b)

A solution of 5b (0.8 g, 1.33 mmol) and CuCl2 (0.214 g, 1.59 mmol) in $CH_2Cl_2$ (20 mL) was stirred for 7 hours at room temperature. The reaction mixture was filtered and filtrate was washed with saturated $NaHCO_3$ (20 mL). The organic layer was dried ($Na_2SO_4$), concentrated, and purified by column chromatography to give the title compound 10b; 0.42 g, 75%; $^1$H NMR (CDCl$_3$): δ 7.39–7.35 (m, 10H), 6.96 (s, 1H), 6.31 (s, 1H), 6.05 (s, 1H), 5.23 (s, 1H), 3.81 (s, 3H), 3.55 (d, J=12.3 Hz, 1H), 3.41 (d, J=12.3 Hz, 1H), 1.32 (s, 3H).

EXAMPLE 24

Benzhydryl 2β-(chloromethyl)-6-[(Z)-(t-butoxycarbonyl)methylene]penicillinate 1,1-dioxide (11a)

To a solution of sulfide 10a, (400 mg, 0.78 mmol) in $CH_2Cl_2$ (20 mL) and pH 6.4 phosphate buffer solution (20 mL) was added mCPBA (70%, 424 mg, 1.72 mmol). The mixture was stirred at room temperature for 18 hours, and then diluted with $CH_2Cl_2$ (10 mL). The organic layer was washed with $NaHCO_3$ solution (20 mL), dried ($Na_2SO_4$), concentrated and purified by column chromatography to give the title compound 11a; 360 mg, 86%; $^1$H NMR (CDCl$_3$): δ 7.38–7.33 (10H, m), 6.99 (1H, s), 6.53 (1H, s), 5.65 (1H, s), 4.69 (1H, s), 4.23 (1H, d, J=12.1 Hz), 3.96 (1H, d, J=12.1 Hz), 1.51 (9H, s), 1.09 (3H, s)

EXAMPLE 25

Benzhydryl 2β-(chloromethyl)-6-[(Z)-(methoxycarbonyl)methylene]penicillinate 1,1-dioxide (11b)

To a solution of sulfide 10b, (300 mg, 0.73 mmol) in $CH_2Cl_2$(15 mL) and pH 6.4 phosphate buffer solution (15 mL) was added mCPBA (70%, 395 mg, 1.6 mmol). The mixture was stirred at room temperature for 1 8 hours, and then diluted with $CH_2Cl_2$ (10 mL). The organic layer was washed with $NaHCO_3$ solution (20 mL), dried ($Na_2SO_4$), concentrated and purified by column chromatography to give the title compound 11b; 240 mg, 74%; $^1$H NMR (CDCl$_3$): δ 7.38–7.33 (10H, m), 6.98 (1H, s), 6.61 (1H, s), 5.49 (1H, s), 4.87 (1H, s), 3.97 (1H, d, J=12.3 Hz), 3.86 (s, 3H), 3.80 (1H, d, J=12.3 Hz), 1.32 (3H, s).

EXAMPLE 26

Disodium salt of 2β-(chloromethyl)-6-[(Z)-carboxymethylene]penicillinate 1,1-dioxide (12c)

To a solution of sulfone 11a, (300 mg, 0.55 mmol) in anisole (1.8 mL, 16.5 mmol) at 0° C. was added trifluoroacetic acid (5.1 mL, 66.0 mmol) over 5 minutes under argon. The reaction mixture was stirred for 10 minutes at 0° C. Excess TFA and anisole were removed in vacuo. The residue was again dissolved in EtOAc (25 mL) and treated with aqueous $NaHCO_3$ (70 mg solid, 0.825 mmol, dissolved in 10 mL $H_2O$) and aqueous layer was purified on a column of CHP20P (Mitsubishi Chemical Corporation) (deionized water as eluent) to give the title compound 12c; 65 mg; $^1$H NMR (D$_2$O): δ 6.54 (1H, s), 5.87 (1H, s), 4.31 (1H, s), 4.05 (2H, ABq, J=12.1 Hz), 1.39 (3H, s).

EXAMPLE 27

Sodium salt of 2β-(chloromethyl)-6-[(Z)-(t-butoxycarbonyl)methylene]-penicillinic acid 1,1 dioxide (12a)

The column described in Example 26 was further eluted (7% EtOH in water) to give the title compound 12a; 50 mg; $^1$H NMR (D$_2$O): δ 6.54 (1H, s), 6.02 (1H, s), 4.39 (1H, s), 4.08 (2H, ABq, J=12.1 Hz), 1.47 (9H, s), 1.41 (3H, s).

EXAMPLE 28

Sodium salt of 2β-(chloromethyl)-6-[(Z)-(methoxycarbonyl)methylene]-penicillanic acid 1,1 dioxide (12b)

To a solution of sulfone 11b, (280 mg, 0.629 mmol) in anisole (2.1 mL, 18.9 mmol) at 0° C. was added trifluoroacetic acid (5.82 mL, 75.5 mmol) over 5 minutes under argon. The reaction mixture was stirred for 15 minutes at 0° C. Excess TFA and anisole were removed in vacuo. The residue was again dissolved in EtOAc (20 mL) and treated with aqueous $NaHCO_3$ (5%, 20 mL) and aqueous layer was purified on a column of CHP20P (Mitsubishi Chemical Corporation) (4% EtOH in deionized water as eluent) to give the title compound 12b; 123 mg, 62%; $^1$H NMR (D$_2$O): δ 6.72 (1H, s), 5.84 (1H, s), 4.45 (1H, s), 4.19 (1H, d, J=12.4 Hz), 4.08 (1H, d, J=12.4 Hz, 1H), 3.76 (3H, s), 1.60 (3H, s).

EXAMPLE 29

Benzhydryl 2β-(hydroxymethyl)-6-[(Z)-(t-butoxycarbonyl)methylene]penicillinate (13)

Chloroacetate 6b (1.9 g, 3.33 mmol) was dissolved in DMF (4 mL) and cooled to 0° C. Pyridine (1.47 mL, 18.3 mmol) was added. Thiourea (0.76 g, 9.99 mmol) was added to the solution and it was stirred at 0°C. until all the thiourea was dissolved. The ice bath was then removed and the reaction allowed to reach room temperature. The volatiles were then removed in vacuo and the residue dissolved in EtOAc (30 mL). This solution was then washed with water (50 mL), dried ($Na_2SO_4$), and concentrated to produce alcohol 13 (1.48 g, 90%) which was used in Example 30 without further purification; $^1$H NMR (CDCl$_3$): δ 87.39–7.29 (m, 10H), 6.95 (s, 1H), 6.16 (s, 1H), 5.99 (s, 1H), 4.99 (s, 1H), 3.49 (d, J=11.6 Hz, 1H), 3.40 (d, J=11.6 Hz, 1H), 1.49 (s, 9H), 1.26 (s, 3H).

EXAMPLE 30

Benzhydryl 2β-(formyl)-6-[(Z)-(t-butoxycarbonyl)methylene]penicillinate (14)

A solution of oxalyl chloride (0.264 mL, 3.03 mmol) in $CH_2Cl_2$ (16 mL) was cooled to −78° C. and anhydrous DMSO (0.267 mL 3.43 mmol) was added dropwise. the solution was stirred at −78° C. for 15 minutes, then a solution of alcohol 13 in CH$_2$Cl$_2$ (5 mL) was added dropwise. The reaction mixture was stirred for 3 hours at −78° C. and then triethylamine (0.983 mL, 7.07 mmol) was added. The reaction mixture was allowed to reach −10° C. The reaction was then quenched with 1N HCl (0.5 mL) and the organic layer was washed with water (30 mL), dried (Na$_2$SO$_4$), and concentrated to produce aldehyde 14 in quantitative yield which was used in Example 31 without further purification; $^1$H NMR (CDCl$_3$): δ 9.09 (s, 1H), 7.38–7.31 (m, 10H), 6.97 (s, 1H), 6.14 (s, 1H), 6.02 (s, 1H), 5.41 (s, 1H), 1.51 (s, 9H), 1.27 (s, 3H).

EXAMPLE 31

Benzhydryl 2β-[(E/Z)-(cyanoethenyl)]-6-[(Z)-(t-butoxycarbonyl)methylene]penicillinate (15)

A solution of aldehyde 14 (1 g, 2.03 mmol) in acetonitrile (10 mL) was added dropwise at −20° C. to a suspension of cyanomethylenetriphenylphosphorane (0.61 g, 2.03 mmol) and 0.4 M LiClO$_4$ in acetonitrile (10 mL). After 4 hours, the solvent was evaporated and the residue dissolved in EtOAc (50 mL). The organic layer was washed with water (50 mL), dried (Na$_2$SO$_4$), concentrated and purified by column chromatography to give the title compound 15; 0.41 g, 40%; $^1$H NMR (CDCl$_3$): (major Z isomer) δ 7.41–7.38 (m, 10H), 6.99 (s, 1H), 6.48 (d, J=11.9 Hz, 1H), 6.23 (s, 1H), 6.09 (s, 1H), 5.39 (d, J=11.9 Hz, 1H), 4.99 (s, 1H), 1.54 (s, 3H), 1.53 (s, 9H).

EXAMPLE 32

Benzhydryl 2β-[(E/Z)-(cyanoethenyl)]-6-[(Z)-(t-butoxycarbonyl)methylene]penicillin-ate 1,1-dioxide (16)

To a solution of sulfide 15 (0.35 g, 0.678 mmol) in CH$_2$Cl$_2$ (10 mL) was added mCPBA (70%, 0.37 g, 1.49 mmol) in one portion followed by pH 6.4 phosphate buffer solution (10 mL) and the reaction mixture was stirred overnight. The organic layer was separated, washed with saturated aqueous NaHCO$_3$ (1×20 mL), dried (Na$_2$SO$_4$), concentrated and purified by silica gel chromatography to give the title compound 16; 0.240 g, 65%; $^1$H NMR (CDCl$_3$): (major isomer) δ 7.38–7.27 (10H, m), 6.98 (1H, s), 6.59 (1H, s), 6.43 (d, J=16.4 Hz, 1H), 5.53 (s, 1H), 5.35 (d, J=16.4 Hz, 1H), 4.67 (s, 1H), 1.52 (s, 9H), 1.51 (s, 3H).

EXAMPLE 33

Disodium Salt of 2β-[(E/Z)-(cyanoethenyl)]-6-[(Z)-carboxymethylene]-penicillinate 1,1-dioxide (17)

To a solution of sulfone 16, (240 mg, 0.438 mmol) in anisole (1.43 mL, 13.1 mmol) at 0° C. was added trifluoroacetic acid (4.1 mL, 53.5 mmol) over 5 minutes under argon. The reaction mixture was stirred for 30 minutes at 0° C. Excess TFA and anisole were removed in vacuo. The residue was again dissolved in EtOAc (20 mL) and treated with aqueous NaHCO$_3$ (67 mg solid, 0.79 mmol, dissolved in 10 mL H$_2$O) and aqueous layer was purified on a column of CHP20P (Mitsubishi Chemical Corporation) to give the title compound 17; 60 mg, 37%; $^1$H NMR (D$_2$O): δ 6.73 (d, J=16.3 Hz, 1H), 6.42 (1H, s), 5.73 (d, J=16.3 Hz, 1H), 5.54 (1H, s), 4.16 (1H, s), 1.47 (3H, s).

EXAMPLE 34

Benzhydryl 2β-{[3',4'-di-(4-methoxybenzyloxy)phenyl]acetoxy}-methyl-6-[(Z)-(t-butoxycarbonyl)methylene]penicillinate (6i)

Using a procedure similar to that described in Example 6, except replacing the disulfide 5b and the chloroacetic acid used therein with disulfide 5a and 3,4-di(4-methoxybenzyloxy)phenylacetic acid, the title compound was prepared; $^1$H NMR (CDCl$_3$) δ=7.25–7.36 (m, 15H), 6.48–6.90 (m, 7H), 6.17 (s, 1H), 6.00 (s, 1H), 5.04 (s, 2H), 4.99 (s, 2H), 4.61 (s, 1H), 4.02 (d, J=8.24 Hz, 1H) 3.81 (s, 3H), 3.77 (s, 3H), 3.78 (d, J=8.24 Hz, 1H), 3.55 (s, 2H1), 1.52 (s, 9H), 1.48 (s, 3H).

EXAMPLE 35

Benzhydryl 2β-[3',4'-di-(4-methoxybenizyloxy)phenyl]acetoxy-methyl-6-[(Z)-(t-butoxycarbonyl)methylene]-1,1-dioxopenicillinate (7i)

Using a procedure similar to that described in Example 12, except replacing the compound 6f used therein with the compound 6i, the title compound was prepared; 1H NMR (CDCl$_3$) δ=7.26–7.36 (m, 15H), 6.85–6.89 (m, 8H), 6.48 (s, 1H), 5.46 (s, 1H), 5.03 (s, 4H), 4.78 (s, 1H), 4.54 (d, J=6.98 Hz, 1H), 4.37 (d, J=6.98 Hz, 1H), 3.80 (s, 6H), 3.53 (s, 2H), 1.55 (s, 3H), 1.53 (s, 9H).

EXAMPLE 36

Disodium Salt of 2β-[(3',4'-Dihydroxyphenyl)acetoxy]methyl-6-[(Z)-carboxymethylene]-1,1-dioxopenicillinate (8i)

Using a procedure similar to that described in Example 21, except replacing the compound 7h used therein with compound 7i, the title compound was prepared; 1H NMR (CDCl$_3$) δ=6.53–6.77 (m, 4H), 5.77 (s, 1H), 4.41 (d, J=8.24 Hz, 1H), 3.54 (s, 2H), 1.40 (s, 3H).

EXAMPLE 37

Sodium 2β-(acetoxymethyl)-1,1-dioxo-6-[(Z)-2'-pyridylmethylene]penicillinate (29a)

A solution of benzyl ester 28a (330 mg, 0.702 mmol) and LiI (376 mg, 2.81 mmol) in EtOAc (15 mL) was heated to reflux for 12 hours. The reaction mixture was cooled to room temperature, diluted with EtOAc (25 mL) and extracted with 5% NaHCO$_3$ solution (20 mL). The aqueous layer was loaded onto a column of CHP20P (Mitsubishi Chemical Corporation) and compound 29a (123 mg, 44%) was eluted with 5–10% EtOH-H$_2$O; $^1$H NMR (D$_2$O): δ 8.57 (d, J=4.5 Hz, 1H), 7.81 (m, 1H), 7.52 (d, J=7.69 Hz, 1H), 7.42 (s, 1H), 7.37 (m, 1H), 5.98 (s, 1H), 4.60 (d, J=12.3 Hz, 1H), 4.45 (m, 2H), 2.04 (s, 3H), 1.51 (s, 3H).

The intermediate compound 28a was prepared as follows.

a. 4-(2'-Benzothiazolyldithio)-3-[(allyloxycarbonyl)amino]-1-[1'-benzyloxycarbonyl-2'-methylprop-2'-enyl]azetidin-2-one (22a).

A solution of sulfoxide 21a (48 g, 0.118 mol) and 2-mercaptothiazole (19.8 g, 0.118 mol) in toluene (1.5 L) was heated to reflux for 3.5 hours. Toluene was removed under reduced pressure to obtain the disulfide 22a in quantitative yield; $^1$H NMR (CDCl$_3$) δ=7.72 (1H, d, J=8.1 Hz), 7.58 (1H, d, J=8.1 Hz), 7.69–7.25 (7H, m), 6.09 (1H, bd, J=10.7 Hz), 5.65 (1H, m), 5.35 (1H, d, J=4.4 Hz), 5.14–4.94 (4H, m), 4.85 (1H, s), 4.77 (1H, s), 4.41 (2H, m), 1.89 (3H, s).

b. Benzyl 2β-(acetoxymethyl)-6-[(allyloxycarbonyl)amino]penicillinate (23a).

A mixture of disulfide 22a (9.0 g, 16.2 mmol), acetic acid (40 mL, 697.3 mmol), and silver acetate (5.6 g, 33.7 mmol) in CH$_2$Cl$_2$ (350 mL) was stirred for 4 hours at room temperature. The reaction mixture was filtered and the filtrate washed with 10% NaHCO$_3$ solution (500 mL). The organic layer was dried over Na$_2$SO$_4$, concentrated, and purified by silica gel chromatography to yield a 4:1 mixture of cepham 24a and penam 23a (yield 6.4 g, 88.3%); $^1$H NMR (CDCl$_3$): δ 7.37 (bs, 5H), 5.92 (m, 2H), 5.61 (d, J=4.16 Hz, 1H), 5.43 (m, 1H), 5.35–5.17 (m, 4H), 4.69 (s, 1H), 4.61 (bd, 2H), 4.37 (d, J=11.6 Hz, 1H), 3.80 (d, J=11.6 Hz, 1H), 2.11 (s, 3H), 1.41 (s, 3H).

c. Benzyl 2β-(acetoxymethyl)-6-aminopenicillinate (25a).

To a solution of carbamate 23a (6.0 g, 13.42 mmol), acetic acid (1.8 mL, 32.2 mmol), and Pd(PPh$_3$)$_4$ (310 mg, 0.268 mmol) in CH$_2$Cl$_2$ (600 mL) was added tributyltin hydride (3.98 mL, 14.8 mmol) and the reaction was stirred for 30 minutes at room temperature. The reaction mixture was washed with NaHCO$_3$ solution (200 mL) and dried over Na$_2$SO$_4$. Purification by silica gel chromatography yielded amine 25a (3.25 g, 66.7%); $^1$H NMR (CDCl$_3$): δ 7.37–7.32 (m, 5H), 5.55 (d, J=4.20 Hz, 1H), 5.19 (m, 2H), 4.70 (s, 1H), 4.53 (d, J=4.20 Hz, 1H), 4.23 (d, J=11.5 Hz, 1H), 3.87 (d, J=11.5 Hz, 1H), 2.06 (s, 3H), 1.35 (s, 3H).

d. Benzyl 2β-(acetoxymethyl)-6-oxopenicillinate (26a).

To a solution of amine 25a (2.2 g, 6.06 mmol) in EtOAc (50 mL) was added isopropyl nitrite (2.03 mL, 9.09 mmol, 40% solution in CH$_2$Cl$_2$) followed by trifluoroacetic acid (0.014 mL, 0.18 mmol). The reaction mixture was stirred for 30 minutes at room temperature. Volatiles were removed in vacuo and the yellow solid was dissolved in C$_6$H$_6$ (10 mL). To this solution was added propylene oxide (20 mL) followed by Rh$_2$(OOct)$_4$ (15 mg) and the reaction mixture was stirred for 20 minutes at room temperature. Volatiles were removed to obtain the ketone 26a (2.2 g, quantitative); $^1$H NMR (CDCl$_3$): δ 7.39–7.36 (m, 5H), 5.77 (s, 1H), 5.22 (s, 2H), 5.02 (s, 1H), 4.09 (d, J=11.9 Hz, 1H), 3.84 (d, J=11.9 Hz, 1H), 2.07 (s, 3H), 1.37 (s, 3H).

e. Benzyl 2β-(acetoxymethyl)-6-[(Z)-2'-pyridylmetlhylene]penicillinate (27a).

To a suspension of triphenyl(2-pyridylmethyl)phosphonium chloride (3.55 g, 9.12 mmol) in dry THF (30 mL) was added NaNH$_2$ (0.31 g, 7.9 mmol) and the reaction mixture was stirred for 1 hour at room temperature. The solution was then allowed to stand motionless (in order to allow the precipitate to settle) for 2 hours. A second solution of ketone 26a (2.2 g, 6.1 mmol) in dry THF (20 mL) was chilled to −78° C. To this ketone solution was carefully added the supernatant solution of the Wittig ylide at −78° C. and the reaction mixture stirred for 40 minutes at the same temperature. The reaction mixture was then quenched with sat NH$_4$Cl solution (50 mL) and extacted with CH$_2$Cl$_2$ (100 mL). The organic layer was dried, concentrated, and purified by silica gel chromatography to produce 27a (1.49 g, 56%); $^1$H NMR (CDC$_3$): δ 8.62 (d, J=4.27 Hz, 1H), 7.69 (m, 1H), 7.42–7.33 (m, 5H), 6.92 (s, 1H), 6.27 (s, 1H), 5.23 (s, 2H), 4.93 (s, 1H), 4.10 (d, J=11.8 Hz, 1H), 3.83 (d, J=11.8 Hz, 1H), 2.07 (s, 3H), 1.27 (s, 3H).

f. Benzyl 2β-(acetoxymethyl)-1,1-dioxo-6-[(Z)-2'-pyridylmiethylene]-penicillinate (28a).

To a solution of sulfide 27a (1.1 g, 2.51 mmol) in CH$_2$Cl$_2$ (30 mL) was added mCPBA (70%, 1.37 g, 5.53 mmol) followed by pH 6.4 phosphate buffer solution (30 mL) and the reaction mixture was stirred overnight at room temperature. The organic layer was separated, washed with 5% NaHCO$_3$ solution (50 mL), dried, concentrated and purified by column chromatography to yield the sulfone 28a (0.78 66.1%); $^1$H NMR (CDCl$_3$): δ 8.68 (d, J=4.28 Hz, 1H), 7.72 (m, 1H), 7.37 (m, 5H), 7.30 (m, 1H), 7.26 (s, 1H), 5.76 (s, 1H), 5.29 (d, J=11.9 Hz, 1H), 5.23 (d, J=11.9 Hz, 1H), 4.69 (s, 1H), 4.57 (d, J=12.0 Hz, 1H), 4.39 (d, J=12.0 Hz, 1H), 2.06 (s, 3H), 1.39 (s, 3H).

The intermediate compounds 20a and 21a (FIG. 8) can be prepared as described by Butynak et. al. *J. Am. Chem. Soc.* 120, 6846–6847 (1998).

EXAMPLE 38

Sodium 1,1-Dioxo-2β-(phenylacetoxy)methyl-6-[(Z)-2'-pyridylmethylene]penicilliniate (29b)

A solution of benzhydryl ester 28b (590 mg, 1.08 mmol) was dissolved in anisole (3.5 mL, 32.4 mmol) and cooled to 0° C. To this solution was added TFA (10 mL, 129.6 mmol) at 0° C. and the reaction was stirred for 20 minutes at the same temperature. Volatiles were removed in vacuo, and the residue was dissolved in ethyl acetate (30 mL) and extracted with 10% NaHCO$_3$ solution (20 mL). The aqueous layer was loaded onto a column of CHP20P (Mitsubishi Chemical Corporation) and compound 29b (298 mg, 69%) was eluted with 5–10% EtOH-H$_2$O; $^1$H NMR (D$_2$O): δ 8.53 (d, J=4.5 Hz, 1H), 7.77 (m, 1H), 7.47 (d, J=7.72 Hz, 1H), 7.33 (m, 2H), 7.24–7.17 (m, 5H), 5.89 (s, 1H), 4.60 (d, J=12.6 Hz 1H), 4.41 (d, J=12.6 Hz, 1H), 4.38 (s, 1H), 3.65 (s, 2H), 1.39 (s, 3H).

The intermediate compound 28b was prepared as follows.

a. 4-(2'-Benzothiazolyldithio)-3-[(allyloxycarbonyl)amino]-1-[1'-benzhydryloxycarbonyl-2'-methylprop-2'-enyl]azetidin-2-one (22b).

To a solution of benzhydryl 6-[(allyloxycarbonyl)amido]penicillinate sulfoxide, 21b, (26.0 g, 53.9 mmol) in toluene (800 mL) was added 2-mercaptobenzothiazole (19.8 g, 53.9 mmol) and the reaction was heated to reflux for 3.5 hours. Volatiles were removed under reduced pressure to give 22b (quantitative yield); $^1$H NMR (CDCl$_3$): δ 7.85 (1H, d, J=8.1 Hz), 7.72 (1H, d, J=8.1 Hz), 7.50–7.10 (12H, m), 6.90 (1H, s), 6.15 (1H, bd, J=10.5 Hz), 5.85 (1H, m), 5.50 (1H, d, J=4.4 Hz), 5.35–5.17 (3H m), 5.12 (1H, s), 5.02 (1H, s), 4.95 (1H, s), 4.55 (2H, m), 1.89 (3H, s).

b. Benzhydryl 2-(phenylacetoxy)methyl-6-[(allyloxycarbonyl)amino]penicillinate (23b).

A mixture of disulfide 22b (6.3 g, 9.99 mmol), phenylacetic acid (58.4 g, 429.3 mmol) and silver acetate (3.47 g, 20.8 mmol) in CH$_2$Cl$_2$(180 mL) was stirred at room temperature for 4 hours. The reaction mixture was filtered and the filtrate was washed with 10% NaHCO$_3$ solution (500 mL). The organic layer was dried over Na$_2$sO$_4$, concentrated and purified by silica gel chromatography to yield a 4:1 mixture of penam 23b and cepham 24b (yield 4.5 g, 75%); $^1$H NMR (CDCl$_3$): δ 7.44–7.26 (m, 15H), 6.93 (s, 1H), 5.95 (m, 1H), 5.87 (bd, 1H), 5.60 (d, J=4.8 Hz, 1H), 5.51 (m, 1H), 5.35 −5.23 (m, 2H), 4.71 (s, 1H), 4.61 (bd, 2H), 4.34 (d, J=11.6 Hz, 1H), 3.83 (d, J=11.8 Hz, 1H), 2.16 (s, 3H), 1.19 (s, 3H).

c. Benzhydryl 2β-(phenylacetoxy)methyl-6-aminopenicillinate (25b).

To a solution of carbamate 23b (4.5 g, 7.5 mmol), acetic acid (1.02 mL, 17.98 mmol) and Pd(Ph$_3$P)$_4$ (172 mg, 1.5 mmol) in CH$_2$Cl$_2$ (450 mL) was added (n-Bu)$_3$SnH (2.21 mL, 8.24 mmol) and the reaction was stirred for 30 minutes at room temperature. The reaction mixture was washed with NaHCO$_3$ solution (200 mL), and the organic layer was dried, concentrated, and purified by silica gel chromatography to give amine 25b (2.3 g, 70%); $^1$H NMR (CDCl$_3$): δ 7.36–7.24 (m, 15H, 6.93 (s, 1H), 5.56 (d, J=4.24 Hz, 1H), 4.75 (s, 1H), 4.53 (d, J=4.24 Hz, 1H), 4.26 (d, J=11.5 Hz, 1H), 4.00 (d, J=11.5 Hz, 1H), 3.68 (q, 2H), 1.18 (s, 3H).

d. Benzhydryl 2β-(phenylacetoxy)methyl-6-oxopenicillinate (26b).

To a solution of amine 25b (2.0 g, 4.45 mmol) in EtOAc (40 mL) was added isopropyl nitrite (1.52 mL, 6.83 mmol, 40% solution in CH$_2$I$_2$) followed by trifluoroacetic acid (0.010 mL, 0.14 mmol). The reaction mixture was stirred for 30 minutes at room temperature. Volatiles were removed in vacuo and the yellow solid was dissolved in benzene (10 mL). To this solution was added propylene oxide (20 mL) followed by Rh$_2$(OOct)$_4$ (15 mg) and the reaction mixture was stirred for 20 minutes at room temperature. Volatiles were removed to obtain the ketone 26b (2.0 g, quantitative); $^1$H NMR (CDCl$_3$): δ 7.39–7.27 (m, 15H 1H), 6.97 (s, 1H), 5.81 (s, 1H), 5.08 (s, 1H), 4.14 (d, J=11.9 Hz, 1H), 3.80 (d, J=11.9 Hz, 1H), 3.64 (q, 2H), (s, 3H).

e. Benzhydryl 2β-(phenylacetoxy)methyl-6-[(Z)-2'-pyridylmethylene]penicillinate (27b).

To a suspension of triphenyl(2-pyridylmethyl) phosphonium chloride (2.67 g, 6.84 mmol) in dry THF (20 mL) was added NaNH$_2$ (0.23 g, 5.94 mmol) and the reaction mixture was stirred for 1 hour at room temperature. The solution was then allowed to stand motionless (in order to allow the precipitate to settle) for 2 hours. A second solution of ketone 26b (2.0 g, 4.57 mmol) in dry THF (20 mL) was chilled to −78° C. To this ketone solution was carefully added the supernatant solution of the Wittig ylide at −78° C. and the reaction mixture stirred for 40 minutes at the same temperature. The reaction mixture was then quenched with sat NH$_4$Cl solution (50 mL) and extacted with CH$_2$Cl$_2$ (100 mL). The organic layer was dried, concentrated, and purified by silica gel chromatography to produce 27b (760 mg, 32%); $^1$H NMR (CDCl$_3$): δ 8.64 (d, J=4.18 Hz, 1H), 7.70 (m, 1H), 7.40–7.21 (m, 17H), 6.97 (s, 1H), 6.94 (s, 1H), 6.28 (s, 1H), 4.97 (s, 1H), 4.12 (d, J=11.8 Hz, 1H), 3.82 (d, J=11.8 Hz, 1H), 3.66 (q, 2H), 1.23 (s, 3H).

f. Benzhydryl 1,1-dioxo-2β-(phenylacetoxy)methyl-6-[(Z)-2'-pyridylmethylene]penicillinate (28b).

To a solution of sulfide 27b (0.7 g, 1.36 mmol) in CH$_2$Cl$_2$ (30 mL) was added mCPBA (70%, 0.71 g, 2.86 mmol) followed by pH 6.4 phosphate buffer solution (30 mL) and the reaction mixture was stirred overnight at room temperature. The organic layer was separated, washed with 5% NaHCO$_3$ solution (50 mL), dried, concentrated and purified by column chromatography to yield the sulfone 28b (0.595 g, 80 %); $^1$H NMR (CDCl$_3$): δ 8.70 (d, J=3.76 Hz, 1H), 7.73 (m, 1H), 7.36–7.26 (m, 17H), 6.97 (s, 1H), 5.75 (s, 1H), 4.73 (s, 1H), 4.63 (d, J=12.3 Hz, 1H), 4.40 (d, J=12.3 Hz, 1H), 3.65 (s, 2H), 1.15 (s, 3H).

The intermediate compounds 20b and 21b (FIG. 8) can be prepared as described by Buynak et. al. *J. Am. Chem. Soc.* 120, 6846–6847 (1998).

EXAMPLE 39

The following illustrate representative pharmaceutical dosage forms, containing a compound of formula I ('Compound X'), for therapeutic or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

-continued

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |

| (v) Injection 2 (10 mg/ml) | mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |

| (vi) Aerosol | mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

| (vii) Tablet | mg/tablet |
|---|---|
| 'Compound X' | 100.0 |
| β-lactam antibiotic | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 400.0 |

| (viii) Tablet | mg/tablet |
|---|---|
| 'Compound X' | 20.0 |
| β-lactam antibiotic | 10.0 |
| Microcrystalline cellulose | 410.0 |
| Starch | 50.0 |
| Sodium starch glycolate | 15.0 |
| Magnesium stearate | 5.0 |
| | 510.0 |

-continued

| (ix) Capsule | mg/capsule |
|---|---|
| 'Compound X' | 10.0 |
| β-lactam antibiotic | 10.0 |
| Colloidal silicon dioxide | 1.5 |
| Lactose | 465.5 |
| Pregelatinized starch | 120.0 |
| Magnesium stearate | 3.0 |
| | 610.0 |

| (x) Injection 1 (1 mg/ml) | mg/ml |
|---|---|
| 'Compound X' (free acid form) | 1.0 |
| β-lactam antibiotic | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |

The above formulations may be obtained by conventional procedures well known in the pharmaceutical art. The β-lactam antibiotic in the above formulations can be any β-lactam antibiotic, including those identified specifically hereinabove.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I):

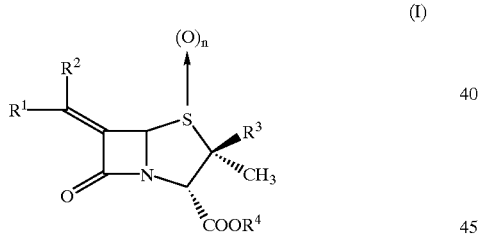

(I)

wherein

R$^1$ and R$^2$ are each independently hydrogen, (C$_1$–C$_{10}$)alkyl, (C$_3$–C$_8$)cycloalkyl, (C$_2$–C$_{10}$)alkenyl, (C$_2$–C$_{10}$)alkynyl, —COOR$_a$, —CONR$_b$R$_c$, cyano, —C(=O)R$_d$, —OR$_e$, aryl, heteroaryl, oxazolidinyl, isoxazolidinyl, morpholinyl, —S(O)$_m$R$_f$, —NR$_g$R$_h$, azido, or halo;

R$^3$ is (C$_3$–C$_{10}$)alkyl, (C$_2$–C$_{10}$)alkenyl, (C$_2$–C$_{10}$)alkynyl, (C$_1$–C$_{10}$)alkanoyl, (C$_3$–C$_8$)cycloalkyl, aryl, heteroaryl, aryl(C$_1$–C$_{10}$)alkyl, heteroaryl(C$_1$–C$_{10}$)alkyl, or —CH$_2$R$_i$, wherein R$_i$ is halo, cyano, cyanato, —OR$_j$, —NR$_k$R$_l$, azido, —SR$_m$, or (C$_3$–C$_8$)cycloalkyl;

R$^4$ is hydrogen, (C$_1$–C$_{10}$)alkyl, (C$_3$–C$_8$)cycloalkyl, (C$_2$–C$_{10}$)alkenyl, (C$_2$–C$_{10}$)alkynyl, aryl, or heteroaryl;

m and n are each independently 0, 1, or 2;

each R$_a$–R$_f$ is independently hydrogen, (C$_1$–C$_{10}$)alkyl, (C$_3$–C$_8$)cycloalkyl, (C$_2$–C$_{10}$)alkenyl, (C$_2$–C$_{10}$)alkynyl, aryl, heteroaryl, oxazolidinyl, isoxazolidinyl, or morpholinyl;

each R$_g$ or R$_h$ is independently hydrogen, (C$_1$–C$_{10}$)alkyl, (C$_3$–C$_8$)cycloalkyl, (C$_2$–C$_{10}$)alkenyl, (C$_2$–C$_{10}$)alkynyl, (C$_1$–C$_{10}$)alkanoyl, aryl, benzyl, phenethyl, heteroaryl oxazolidinyl, isoxazolidinyl, or morpholinyl; or R$_g$ and R$_h$ together with the nitrogen to which they are attached are triazolyl, imidazolyl, oxazolidinyl, isoxazolidinyl, pyrrolyl, morpholino, piperidino, pyrrolidino, pyrazolyl, indolyl, or tetrazolyl;

R$_j$ is hydrogen, (C$_1$–C$_{10}$)alkyl, (C$_3$–C$_8$)cycloalkyl, (C$_2$–C$_{10}$)alkenyl, (C$_2$–C$_{10}$)alkynyl, —C(=O)N(RP)$_2$, aryl, heteroaryl, arylcarbonyl, heteroarylcarbonyl, or (C$_1$–C$_{10}$)alkanoyl, wherein each R$_p$ is independently hydrogen, (C$_1$–C$_{10}$)alkyl, aryl, benzyl, phenethyl, or heteroaryl;

each R$_k$ or R$_l$ is independently hydrogen, (C$_1$–C$_{10}$)alkyl, (C$_3$–C$_8$)cycloalkyl, (C$_2$–C$_{10}$)alkenyl, (C$_2$–C$_{10}$)alkynyl, (C$_1$–C$_{10}$)alkanoyl, —C(=O)N(R$_q$)$_2$, aryl, benzyl, phenethyl, heteroaryl oxazolidinyl, isoxazolidinyl, or morpholinyl, wherein each R$_q$ is independently hydrogen, (C$_1$–C$_{10}$)alkyl, aryl, benzyl, phenethyl, or heteroaryl; or R$_k$ and R$_l$ together with the nitrogen to which they are attached are triazolyl, imidazolyl, oxazolidinyl, isoxazolidinyl, pyrrolyl, morpholino, piperidino, pyrrolidino, pyrazolyl, indolyl, or tetrazolyl; and R$_m$ is hydrogen, (C$_1$–C$_{10}$)alkyl, (C$_3$–C$_8$)cycloalkyl, (C$_2$–C$_{10}$)alkenyl, (C$_2$–C$_{10}$)alkynyl, cyano, aryl, benzyl, phenethyl, heteroaryl, oxazolidinyl, isoxazolidinyl, or morpholinyl;

wherein any (C$_1$–C$_{10}$)alkyl, (C$_3$–C$_8$)cycloalkyl, (C$_2$–C$_{10}$)alkenyl, (C$_2$–C$_{10}$)alkynyl, (C$_1$–C$_{10}$)alkanoyl, aryl, benzyl, phenethyl, heteroaryl, arylcarbonyl, heteroarylcarbonyl, oxazolidinyl, isoxazolidinyl, or morpholinyl of R$^1$–R$^4$, R$_a$–R$_m$, or R$_p$–R$_q$, may optionally be substituted with 1, 2, or 3 Z; and each Z is independently halo, nitro, cyano, hydroxy, (C$_1$–C$_{10}$)alkyl, (C$_3$–C$_8$)cycloalkyl, (C$_1$–C$_{10}$)alkoxy, (C$_1$–C$_{10}$)alkanoyl, (C$_2$–C$_{10}$)alkanoyloxy, trifluoromethyl, aryl, aryloxy, heteroaryl, or —SR$_n$, wherein R$_n$ is hydrogen, (C$_1$–C$_{10}$)alkyl, (C$_3$–C$_8$)cycloalkyl, aryl, benzyl, phenethyl, or heteroaryl;

and further wherein any aryl, aryloxy, heteroaryl, benzyl, or phenethyl of Z may optionally be substituted with 1, 2, or 3 substituents selected from the group consisting of halo, nitro, cyano, hydroxy, (C$_1$–C$_{10}$)alkyl, (C$_3$–C$_8$)cycloalkyl, (C$_1$–C$_{10}$)alkoxy, (C$_1$–C$_{10}$)alkanoyl, (C$_2$–C$_{10}$)alkanoyloxy, benzyloxy, 4-methoxybenzyloxy, and trifluoromethyl;

or a pharmaceutically acceptable salt thereof.

2. A compound of claim 1 wherein any aryl, aryloxy, heteroaryl, benzyl, or phenethyl of Z may optionally be substituted with 1, 2, or 3 substituents selected from the group consisting of halo, nitro, cyano, hydroxy, (C$_1$–C$_{10}$)alkyl, (C$_3$–C$_8$)cycloalkyl, (C$_1$–C$_{10}$)alkoxy, (C$_1$–C$_{10}$)alkanoyl, (C$_2$–C$_{10}$)alkanoyloxy, and trifluoromethyl.

3. The compound of claim 1 wherein R$^1$ is hydrogen.

4. The compound of claim 1 wherein R$^2$ is carboxy, tert-butoxycarbonyl, 2-pyridyl, or methoxycarbonyl.

5. The compound of claim 1 wherein R$^3$ is —CH$_2$R$_i$.

6. The compound of claim 5 wherein R$_i$ is halo, cyano, cyanato, —OR$_j$, —NR$_k$R$_l$, azido, or —SR$_m$.

7. The compound of claim 1 wherein R$^3$ is —CH$_2$OR$_j$.

8. The compound of claim 7 wherein R$_j$ is C$_2$-alkanoyl, optionally substituted with halo, nitro, cyano, hydroxy, (C$_3$–C$_8$)cycloalkyl, (C$_1$–C$_{10}$)alkoxy, (C$_1$–C$_{10}$)alkanoyl, (C$_2$–C$_{10}$)alkanoyloxy, trifluoromethyl, aryl, aryloxy, heteroaryl, or —SR$_n$; and R$_n$ is hydrogen, (C$_1$–C$_{10}$)alkyl, (C$_3$–C$_8$)cycloalkyl, aryl, benzyl, phenethyl, or heteroaryl;

wherein any aryl, aryloxy, heteroaryl, benzyl, or phenethyl may optionally be substituted with 1, 2, or 3 substituents selected from the group consisting of halo, nitro, cyano, hydroxy, $(C_1–C_{10})$alkyl, $(C_3–C_8)$cycloalkyl, $(C_1–C_{10})$ alkoxy, $(C_1–C_{10})$alkanoyl, $(C_2–C_{10})$alkanoyloxy, and trifluoromethyl.

9. The compound of claim 1 wherein $R^3$ is acetoxymethyl, phenylacetoxymethyl, phenoxyacetoxymethyl, chloroacetoxymethyl, pyridylacetoxymethyl, triazolylacetoxymethyl, imidazolylacetoxymethyl, tetrazolylthioacetoxymethyl, or tetrazolylthioacetoxymethyl optionally substituted on the tetrazol ring with $(C_1–C_6)$alkyl, or aryl.

10. The compound of claim 1 wherein $R^3$ is acetoxymethyl, chloroacetoxymethyl, formyloxymethyl, phenylacetoxymethyl, (1-methyl-1H-tetrazol-5-ylthio) acetoxymethyl, (3,4-dihydroxyphenyl)acetoxymethyl, 3,4-di(4-methoxybenzyloxy)phenylacetoxymethyl, chloromethyl, formyl, or 2-cyanovinyl.

11. The compound of claim 1 wherein $R^3$ is acetoxymethyl, chloroacetoxymethyl, phenylacetoxymethyl, (3,4-dihydroxyphenyl)acetoxynmethyl, or (1-methyl-1H-tetrazol-5-ylthio)acetoxymethyl.

12. The compound of claim 1 wherein $R^4$ is hydrogen or diphenylmethyl.

13. The compound benzhydryl 2β-(acetoxymethyl)-6-[(Z)-(t-butoxycarbonyl)-methylene]penicillinate; benzhydryl 2β-(chloroacetoxymethyl)-6-[(Z)-(t-butoxycarbonyl)methylene]penicillinate; benzhydryl 2β-(formyloxymethyl)-6-[(Z)-(t-butoxycarbonyl)methylene]penicillinate; benzhydryl 2β-(phenylacetoxymethyl)-6-[(Z)-(t-butoxycarbonyl)methylene]penicillinate; benzhydryl 2β-(acetoxymethyl)-6-[(Z)-(methoxycarbonyl)-methylene] penicillinate; benzhydryl 2β-(chloroacetoxymethyl)-6-[(Z)-(-ethoxycarbonyl)methylene]penicillinate; benzhydryl 2β-(acetoxymethyl)-6-[(Z)-(t-butoxycarbonyl)methylene] penicillinate-1,1-dioxide; benzhydryl 2β-(chloroacetoxymethyl)-6-[(Z)-(t-butoxycarbonyl)-methylene]penicillinate 1,1-dioxide; benzhydryl 2β-(formyloxymethyl)-6-[(Z)-(t-butoxycarbonyl)methylene] penicillinate 1,1-dioxide; benzhydryl 2β-(phenylacetoxymethyl)-6-[(Z)-(t-butoxycarbonyl)-methylene]penicillinate 1,1-dioxide; benzhydryl 2β-(acetoxymethyl)-6-[(Z)-(methoxycarbonyl)methylene]-penicillinate 1,1-dioxide; benzhydryl 2β-(chloroacetoxymethyl)-6-[(Z)-(methoxycarbonyl)-methylene]penicillinate 1,1-dioxide; benzhydryl 2β-[[(1-methyl-1H-tetrazol-5-yl)thio]acetoxymethyl]-6-[(Z)-(t-butoxycarbonyl)-methylene]penicillinate 1,1-dioxide; benzhydryl 2β-[[(1-methyl-1H-tetrazol-5-yl)thio] acetoxymethyl]-6-[(Z)-(methoxycarbonyl)methylene]-penicillinate 1,1-dioxide; disodium salt of 2β-(acetoxymethyl)-6-[(Z)-carboxymethylene]penicillinic acid-1,1-dioxide; disodium salt of 2β-(chloroacetoxymethyl)-6-[(Z)-carboxymethylene] penicillinate 1,1-dioxide; disodium salt of 2β-(formyloxymethyl)-6-[(Z)-carboxymethylene]-penicillinate 1,1-dioxide; disodium salt of 2β-(phenylacetoxymethyl)-6-[(Z)-carboxymethylene]-penicillinate 1,1-dioxide; sodium salt of 2β-(acetoxymethyl)-6-[(Z)-(methoxycarbonyl) methylene]-penicillinic acid 1,1 dioxide; disodium salt of 2β-[[(1-methyl-f11-tetrazol-5-yl)thio]acetoxymethyl]-6-[(Z)-carboxymethylene]penicillinate 1,1-dioxide; sodium salt of 2β-[[(1-methyl-1H-tetrazol-5-yl)thio] acetoxymethyl]-6-[(Z)-(methoxycarbonyl)methylene] penicillinate 1,1-dioxide; benzhydryl 2β-(chloromethyl)-6-[(Z)-(t-butoxycarbonyl)methylene]penicillinate; benzhydryl 2β-(chloromethyl)-6-[(Z)-(methoxycarbonyl)methylene] penicillinate; benzhydryl 2β-(chloromethyl)-6-[(Z)-(t-butoxycarbonyl)methylene]-penicillinate 1,1-dioxide; benzhydryl 2p3-(chloromethyl)-6-[(Z)-(methoxycarbonyl) methylene]penicillinate 1,1-dioxide; disodium salt of 2β-(chloromethyl)-6-[(Z)-carboxymethylene]penicillinate 1,1-dioxide; sodium salt of 2p3-(chloromethyl)-6-[(Z)-(t-butoxycarbonyl)methylene]penicillinic acid 1,1 dioxide; sodium salt of 2β-(chloromethyl)-6-[(Z)-(methoxycarbonyl)-methylene]penicillanic acid 1,1 dioxide; benzhydryl 2β-(hydroxymethyl)-6-[(Z)-(t-butoxycarbonyl)-methylene]penicillinate; benzhydryl 2β-(formyl)-6-[(Z)-(t-butoxycarbonyl)methylene]penicillinate; benzhydryl 2β-[(E/Z)-(cyanoethenyl)]-6-[(Z)-(t-butoxycarbonyl) methylene]-penicillinate; benzhydryl 2β-[(E/Z)-(cyanoethenyl)]-6-[(Z)-(t-butoxycarbonyl)-methylene] penicillin-ate 1,1-dioxide; disodium salt of 2p3-[(E/Z)-(cyanoethenyl)]-6-[(Z)-carboxymethylene]-penicillinate 1,1-dioxide; benzhydryl 2β-{[3',4'-Di-(p-methoxybenzyloxy)phenyl]acetoxy}-methyl-6-[(Z)-(t-butoxycarbonyl)-methylene]penicillinate; benzhydryl 2β-{[3',4'-di-(p-methoxybenzyloxy)-phenyl]acetoxy}-methyl-6-[(Z)-(t-butoxycarbonyl)-methylene]-1,1-dioxopenicillinate; disodium salt of 2β-[(3',4'-dihydroxyphenyl)-acetoxy] methyl-6-[(z)-carboxymethylene]-1,1-dioxopenicillinate; sodium 2β-(acetoxymethyl)-1,1-dioxo-6-[(Z)-2'-pyridylmiethylene]penicillinate; or sodium 1,1-dioxo-2β-(phenylacetoxy)methyl-6-[(Z)-2'-pyridylmethylene] penicillinate.

14. The compound of claim 1 wherein:

$R^1$ is hydrogen;

$R^2$ is $(C_1–C_{10})$alkyl, —$COOR_a$, —$CONR_bR_c$, cyano, —C(=O)Rd, —OR$d$, aryl, heteroaryl, oxazolidinyl, isoxazolidinyl, morpholinyl, —$S(O)_mR_f$, —$NR_gR_h$, azido, or halo;

$R^3$ is $(C_2–C_{10})$alkenyl, $(C_2–C_{10})$alkynyl, $(C_1–C_{10})$ alkanoyl, or —$CH_2R_i$, wherein $R_i$ is halo, cyano, cyanato, —OR, —$NR_kR_l$, azido, —$SR_m$, or $(C_3–C_8)$ cycloalkyl;

$R^4$ is hydrogen, $(C_1–C_{10})$alkyl, $(C_3–C_8)$cycloalkyl, $(C_2–C_{10})$alkenyl, $(C_2–C_{10})$alkynyl, aryl, or heteroaryl;

m and n are each independently 0, 1, or 2;

each $R_a–R_f$ is independently hydrogen, $(C_1–C_{10})$alkyl, $(C_3–C_8)$cycloalkyl, $(C_2–C_{10})$alkenyl, $(C_2–C_{10})$alkynyl, aryl, or heteroaryl;

each $R_g$ or $R_h$ is independently hydrogen, $(C_1–C_{10})$alkyl, $(C_3–C_8)$cycloalkyl, $(C_2–C_{10})$alkenyl, $(C_2–C_{10})$alkynyl, $(C_1–C_{10})$alkanoyl, aryl, benzyl, phenethyl, or or $R_g$ and $R_h$, together with the nitrogen to which they are attached are morpholino, piperidino, or pyrrolidino;

$R_j$ is hydrogen, $(C_1–C_{10})$alkyl, $(C_3–C_8)$cycloalkyl, $(C_2–C_{10})$alkenyl, $(C_2–C_{10})$alkynyl, —C(=O)N(R,)$_2$, aryl, heteroaryl, arylcarbonyl, heteroarylcarbonyl, or $(C_1–C_{10})$alkanoyl, wherein each $R_p$ is independently hydrogen, $(C_1–C_{10})$alkyl, aryl, benzyl, phenethyl, or heteroaryl;

each $R_k$ or $R_l$ is independently hydrogen, $(C_1–C_{10})$alkyl, $(C_1–C_{10})$alkanoyl, aryl, benzyl, or phenethyl; or $R_k$ and $R_l$ together with the nitrogen to which they are attached are morpholino, piperidino, or pyrrolidino; and $R_m$ is hydrogen, $(C_1-C_{10})$alkyl, $(C_3-C_8)$cycloalkyl, $(C_2-C_{10})$alkenyl, or $(C_2-C_{10})$alkynyl;

wherein any $(C_1-C_{10})$alkyl, $(C_1-C_{10})$alkanoyl, aryl, benzyl, phenethyl, heteroaryl, arylcarbonyl, or heteroarylcarbonyl of $R^1$–$R^4$, $R_a$–$R_m$, or $R_p$, may optionally be substituted with 1, 2, or 3 Z; and each Z is independently halo, nitro, cyano, hydroxy, $(C_1-C_{10})$alkyl, $(C_1-C_{10})$alkoxy, $(C_1-C_{10})$alkanoyl, $(C_2-C_{10})$alkanoyloxy, trifluoromethyl, aryl, aryloxy, heteroaryl, or —$SR_n$, wherein $R_n$ is hydrogen, $(C_1-C_{10})$alkyl, $(C_3-C_8)$cycloalkyl, aryl, benzyl, phenethyl, or heteroaryl;

and further wherein any aryl, aryloxy, or heteroaryl, of Z may optionally be substituted with 1, 2, or 3 substituents selected from the group consisting of halo, nitro, cyano, hydroxy, $(C_1-C_{10})$alkyl, $(C_1-C_{10})$alkoxy, $(C_1-C_{10})$alkanoyl, $(C_2-C_{10})$alkanoyloxy, and trifluoromethyl.

15. A pharmaceutical composition comprising a compound of claim 1 in combination with a pharmaceutically acceptable carrier.

16. A method for inhibiting a β-lactamase comprising contacting said β-lactamase with an effective amount of a compound of claim 1.

17. The method of claim 16 wherein the β-lactamase is contacted with the compound in vitro.

18. The method of claim 16 wherein the β-lactamase is contacted with the compound in vivo.

19. A therapeutic method for inhibiting a β-lactamase in a mammal in need of such therapy, comprising administering an effective inhibitory amount of a compound of claim 1 to said mammal.

20. The method of claim 19 wherein the mammal is a human.

\* \* \* \* \*

UNITED STATES PATENT AND TRADEMARK OFFICE
CERTIFICATE OF CORRECTION

PATENT NO.: 6,156,745
DATED: Dec. 5, 2000
INVENTOR(S): Buynak et al.

It is certified that error appears in the above-identified patent and that said Letters Patent is hereby corrected as shown below:

In column 6, line 45, delete "($C_1C_{10}$alkanoyl" and insert --($C_1$-$C_{10}$)alkanoyl--, therefor.

In column 6, line 45, delete one occurrence of "or".

In column 10, line 31, delete "Prefered" and insert --Preferred--, therefor.

In column 10, line 35, delete "coresponding" and insert --corresponding--, therefor.

In column 13, lines 45-46, delete the paragraph break after "in vivo."

In column 13, line 54, delete "arc" and insert --are--, therefor.

In column 16, line 48, delete "2p-" and insert --2β- --, therefor.

In column 18, line 41, insert --*t*-- between "-(" and "-butoxycarbonyl)".

In column 19, line 24, delete "phrase" and insert --phase--, therefor.

In column 21, line 48, insert a hyphen between "methylene]" and "penicillinate".

In column 21, line 54, delete "1 8 hours" and insert --18 hours--, therefor.

In column 24, line 11, delete "methoxybenizyloxy" and insert --methoxybenzyloxy--, therefor.

In column 27, line 1, delete "$CH_2I_2$)" and insert --$CH_2Cl_2$)--, therefor.

In column 30, line 8, delete "$N(RP)_2$" and insert --$N(R_p)_2$--, therefor.

In column 31, line 36, delete "(-ethoxycarbonyl)" and insert --(methoxycarbonyl)--, therefor.

UNITED STATES PATENT AND TRADEMARK OFFICE
CERTIFICATE OF CORRECTION

PATENT NO.: 6,156,745
DATED: Dec. 5, 2000
INVENTOR(S): Buynak et al.

It is certified that error appears in the above-identified patent and that said Letters Patent is hereby corrected as shown below:

In column 31, line 63, delete "f11" and insert --1H--, therefor.

In column 32, line 5, delete "2p3" and insert --2β--, therefor.

In column 32, line 9, delete "2p3" and insert --2β--, therefor.

In column 32, line 20, delete "2p3" and insert --2β--, therefor.

In column 32, line 29, delete "(z)" and insert --(Z)--, therefor.

In column 32, line 37, delete "-C(=O)Rd, -OR$d$" and insert -- -C(=O)$R_d$, -$OR_c$ --, therefor.

In column 32, line 42, delete "-OR," and insert -- -$OR_j$, --, therefor.

In column 32, line 54, delete one occurence of "or".

In column 32, line 58, delete "-C(=O)N(R,)$_2$" and insert -- -C(=O)N($R_p$)$_2$--, therefor.

Signed and Sealed this

Twenty-fourth Day of April, 2001

Attest:

NICHOLAS P. GODICI

Attesting Officer

Acting Director of the United States Patent and Trademark Office